(12) United States Patent
Moussa

(10) Patent No.: US 9,393,244 B2
(45) Date of Patent: Jul. 19, 2016

(54) INCREASING PARKIN ACTIVITY BY ADMINISTERING A DEUBIQUITINATING ENZYME INHIBITOR

(71) Applicant: Georgetown University, Washington, DC (US)

(72) Inventor: Charbel Moussa, Germantown, MD (US)

(73) Assignee: Georgetown University, Washington, DC (US)

(*) Notice: Subject to any disclaimer, the term of this patent is extended or adjusted under 35 U.S.C. 154(b) by 0 days.

(21) Appl. No.: 14/212,750

(22) Filed: Mar. 14, 2014

(65) Prior Publication Data

US 2014/0271668 A1   Sep. 18, 2014

Related U.S. Application Data

(60) Provisional application No. 61/794,338, filed on Mar. 15, 2013.

(51) Int. Cl.
| | | |
|---|---|---|
| *A61K 31/517* | (2006.01) | |
| *A01N 43/54* | (2006.01) | |
| *A61K 38/00* | (2006.01) | |
| *A61K 31/496* | (2006.01) | |
| *A61K 31/506* | (2006.01) | |

(52) U.S. Cl.
CPC ........... *A61K 31/517* (2013.01); *A61K 31/496* (2013.01); *A61K 31/506* (2013.01)

(58) Field of Classification Search
CPC .. A61K 31/496; A61K 31/506; A61K 31/517
USPC ............... 514/17.7, 17.8, 19.3, 44 A, 266.4
See application file for complete search history.

(56) References Cited

U.S. PATENT DOCUMENTS

| | | | |
|---|---|---|---|
| 7,595,306 B2* | 9/2009 | Bumcrot | 514/44 R |
| 2007/0135439 A1 | 6/2007 | Guedat et al. | |
| 2011/0237644 A1 | 9/2011 | Geneste et al. | |
| 2012/0258975 A1 | 10/2012 | Yuan et al. | |
| 2015/0087653 A1* | 3/2015 | Moussa | 514/253.06 |

OTHER PUBLICATIONS

Lonskaya et al., "Tyrosine kinase inhibition increases functional parkin-Beclin-1 interaction and enhances amyloid clearance and cognitive performance", Published online Apr. 7, 2013, EMBO Molecular Medicine, vol. 5, Issue 8, pp. 1247-1262.*
Burns et al., "Parkin promotes intracellular Abeta1-42 clearance," *Hum. Mol. Genet.* 18 3206-3216 (2009).
Lee et al. "A High-Throughput Screening Method for Identification of Inhibitors of the Deubiquitinating Enzyme USP14," *Curr. Protoc. Chem. Biol.* 4: 311-330 (2012).
Liu, et al., "Beclin1 Controls the Levels of p53 by Regulating the Deubiquitination Activity of USP10 and USP13," Cell 147(1):223-234 (2011).
Morrison et al. "A simple cell based assay to measure Parkin activity," *J. Neurochem.* 116(3): 342-9 (2011).
Schlossmacher and Shimura, "Parkinson's disease: assays for the ubiquitin ligase activity of neural Parkin," *Methods Mol. Biol.* 301: 351-69 (2005).
Tian et al. "Characterization of selective ubiquitin and ubiquitin-like protease inhibitors using a fluorescence-based multiplex assay format," *Assay Drug Dev. Technol.* 9(2): 165-173 (2011).

* cited by examiner

*Primary Examiner* — My-Chau T Tran
(74) *Attorney, Agent, or Firm* — Kilpatrick Townsend & Stockton, LLP

(57) ABSTRACT

Provided herein are methods of promoting parkin activity in a subject, comprising: selecting a subject with a disorder associated with decreased Parkin activity; and administering to the subject an effective amount of a composition that increases parkin activity, wherein the composition is an inhibitor of a deubiquitinating enzyme.

8 Claims, 31 Drawing Sheets

INCREASING PARKIN ACTIVITY BY ADMINISTERING A DEUBIQUITINATING ENZYME INHIBITOR

This application claims the benefit of U.S. Application No. 61/794,338, filed on Mar. 15, 2013, which is hereby incorporated in its entirety by this reference.

STATEMENT REGARDING FEDERALLY FUNDED RESEARCH

This invention was made with government support under grant number AG30378 awarded by the National Institutes of Health. The government has certain rights in the invention.

BACKGROUND

Neurodegenerative diseases include genetic and sporadic disorders associated with progressive nervous system dysfunction. It has been estimated that one of four Americans will develop a neurodegenerative condition in their lifetimes. Generally, however, the underlying mechanisms causing the conditions are not well understood and few effective treatment options are available for preventing or treating neurodegenerative diseases. Similarly, treatment options for myodegenerative disease and prion disease are also limited.

SUMMARY

Provided herein is a method of promoting parkin activity in a subject, comprising: selecting a subject with a disorder associated with decreased parkin activity; and administering to the subject an effective amount of a composition that increases parkin activity, wherein the composition is an inhibitor of a deubiquitinating enzyme.

Further provided is a method of treating or preventing a neurodegenerative disease, a myodegenerative disease or prion disease in a subject, comprising: selecting a subject with a neurodegenerative disease of the central nervous system, a myodegenerative disease, a prion disease or at risk for a neurodegenerative disease of the central nervous system, a myodegenerative disease or a prion disease; and administering to the subject an effective amount of a composition that increases parkin activity, wherein the composition is an inhibitor of a deubiquitinating enzyme.

Also provided is a method of treating or preventing cancer in a subject, comprising selecting a subject with cancer or at risk for cancer; and administering to the subject an effective amount of a composition that increases parkin activity, wherein the composition is an inhibitor of a deubiquitinating enzyme.

7C) daily for 3 weeks. Parkin and ubiquitin specific peptidase 10 (USP10) in Tg-APP mice treated with DMSO (FIG. 7D), 10 mg/kg Nilotinib (FIG. 7E), and 5 mg/kg Bosutinib (FIG. 7F) daily for 3 weeks. Tyrosine kinase inhibition increases the interaction between parkin and USP10 and 13.

Figure 8:
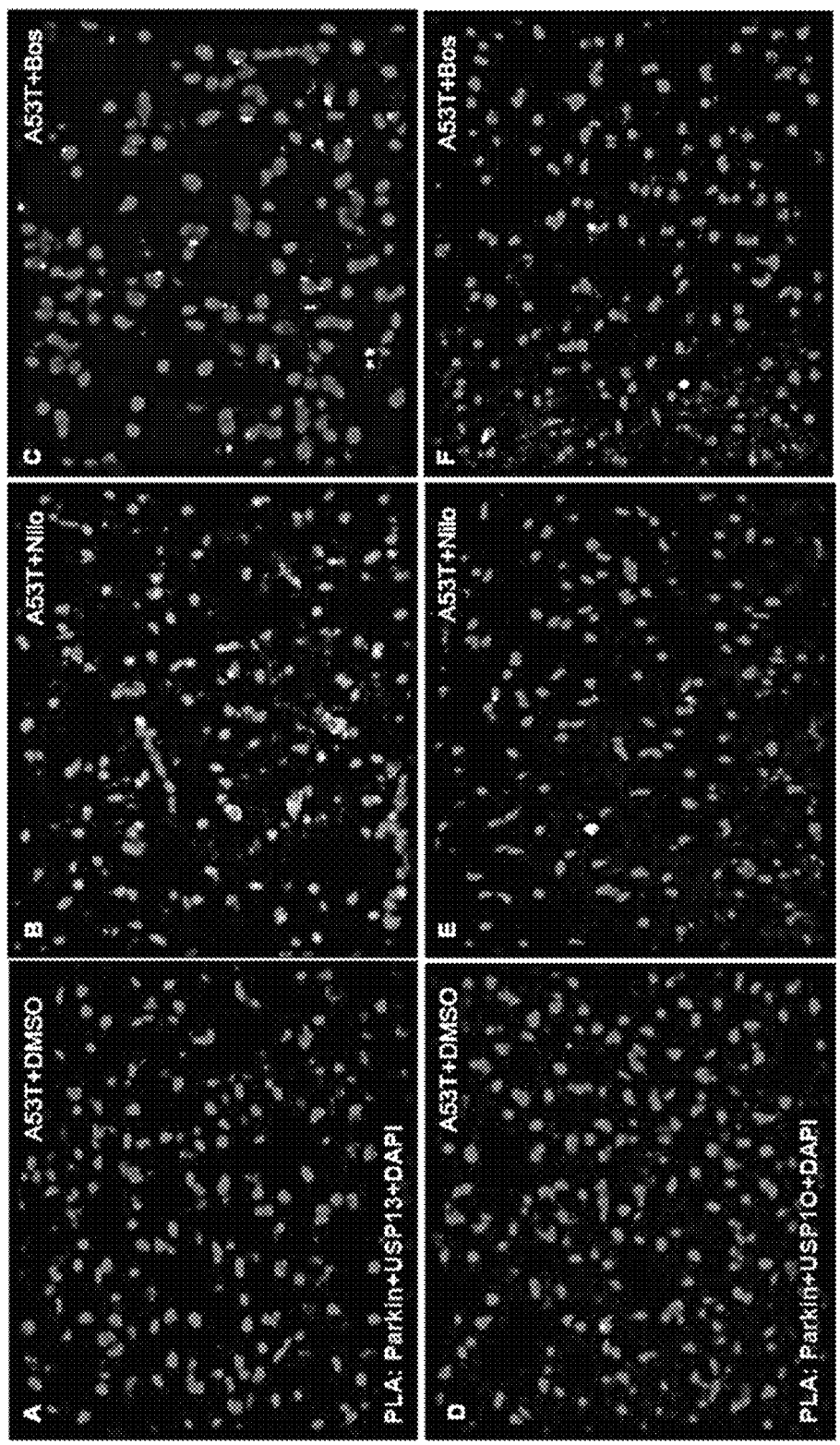

FIG. 8 shows that parkin interaction with deubiquitinating enzymes is decreased in Tg-A53T mice and tyrosine kinase inhibition increases parkin-DUBs interaction. A Proximity Ligation Assay (PLA) in situ on 20 µm thick brain sections shows parkin and ubiquitin specific peptidase 13 (USP13) in A53T mice treated with DMSO (FIG. 8A), 10 mg/kg Nilotinib (FIG. 8B), and 5 mg/kg Bosutinib (FIG. 8C) daily for 3 weeks. Parkin and ubiquitin specific peptidase 10 (USP10) in A53T mice treated with DMSO (FIG. 8D), 10 mg/kg Nilotinib (FIG. 8E), and 5 mg/kg Bosutinib (FIG. 8F) daily for 3 weeks. Tyrosine kinase inhibition increases the interaction between parkin and USP10 and 13.

Figure 9:
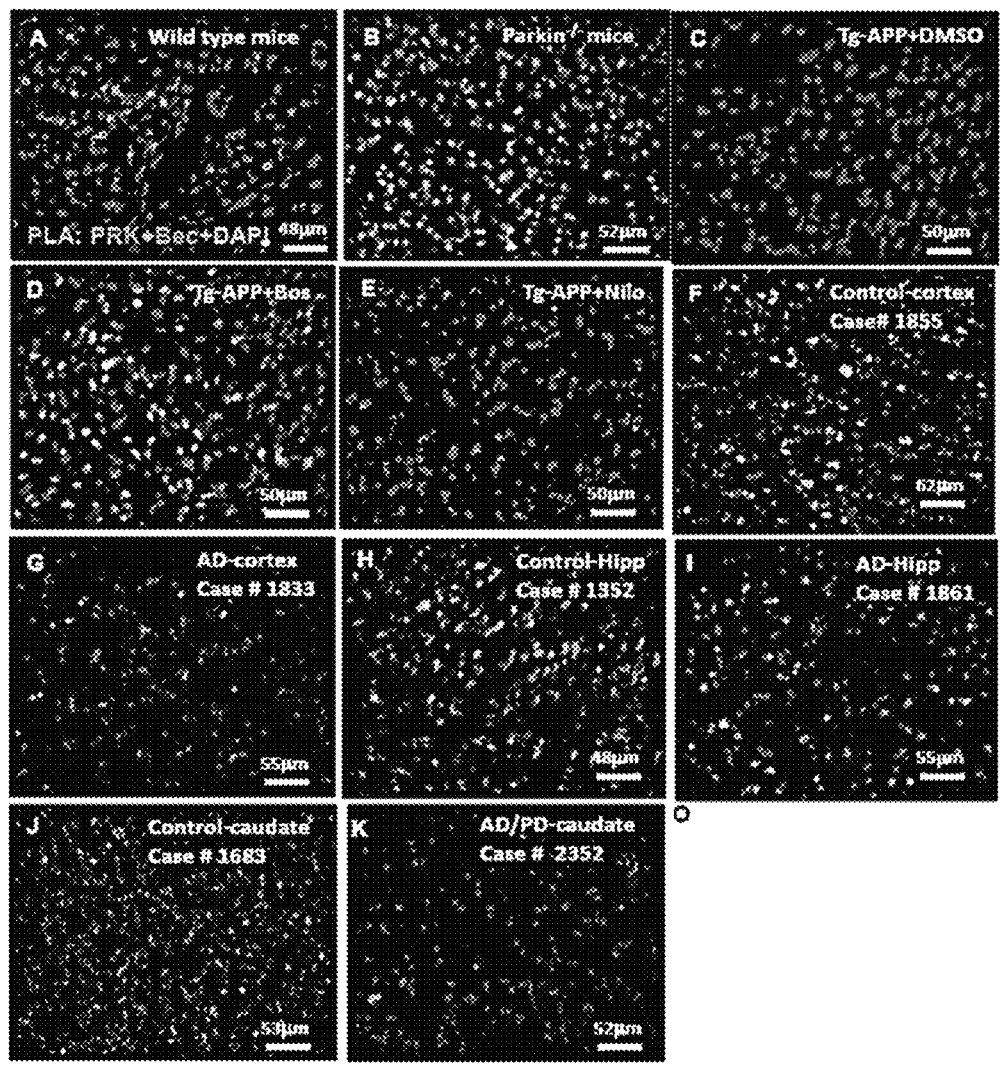

FIG. 9 shows in situ proximity ligation assay (PLA) showing endogenous parkin-beclin-1 complexes in WT C57BL/6 mice (FIG. 9A) (N=5) and parkin−/−mice (FIG. 9B). Also shown is PLA in Tg-APP mice IP injected once daily for 3 weeks with DMSO (FIG. 9C) 5 mg/kg Bosutinib (FIG. 9D) and 10 mg/kg Nilotinib (FIG. 9E) (N=5). Further shown is PLA in human post-mortem brains in the cortex of a normal subject (FIG. 9F) and cortex of an AD patient (FIG. 9G); the hippocampus of a normal subject (FIG. 9H) and of an AD patient (FIG. 9I); the caudate of a normal subject (FIG. 9J) and of an AD/PD patient (FIG. 9K). The increased parkin-USP10/13 interaction is paralleled by decreased parkin-beclin-1 interaction, indicating that DUB deubiquitination of parkin decreases functional parkin-beclin-1 interaction. This data shows that parkin interaction with DUBs, such as ubiquitin specific proteases (USP)-13 and USP-10 regulate parkin activity via deubiquitination.

Figure 10:
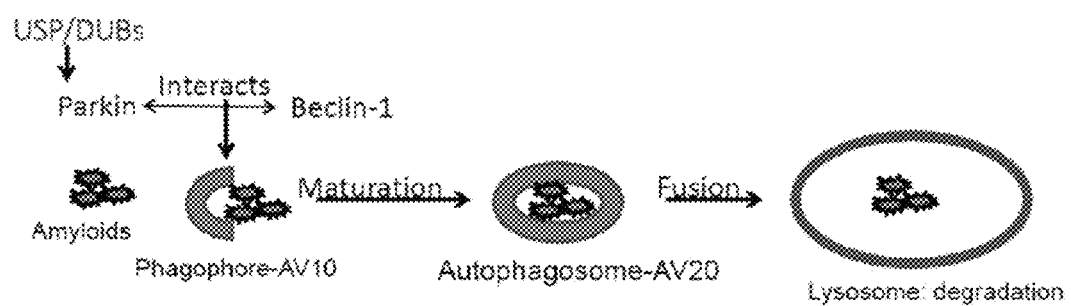

FIG. 10 is a schematic showing that amyloid accumulation leads to autophagic induction and sequestration in phagophores. In transgenic or amyloid expressing animals parkin interaction with beclin-1 is reduced, leading to decreased maturation of phagophore into autophagosomes and autophagic defects. Kinase inhibition activates parkin and increases its interaction with beclin-1, resulting in maturation of phagophores into phagosomes and clearance. Also in human AD and PD brains parkin-beclin-1 interaction is reduced, indicating that USPs inactivate parkin and prevent functional interaction with beclin-1 to execute autophagic clearance of misfolded amyloid proteins.

Figure 11:
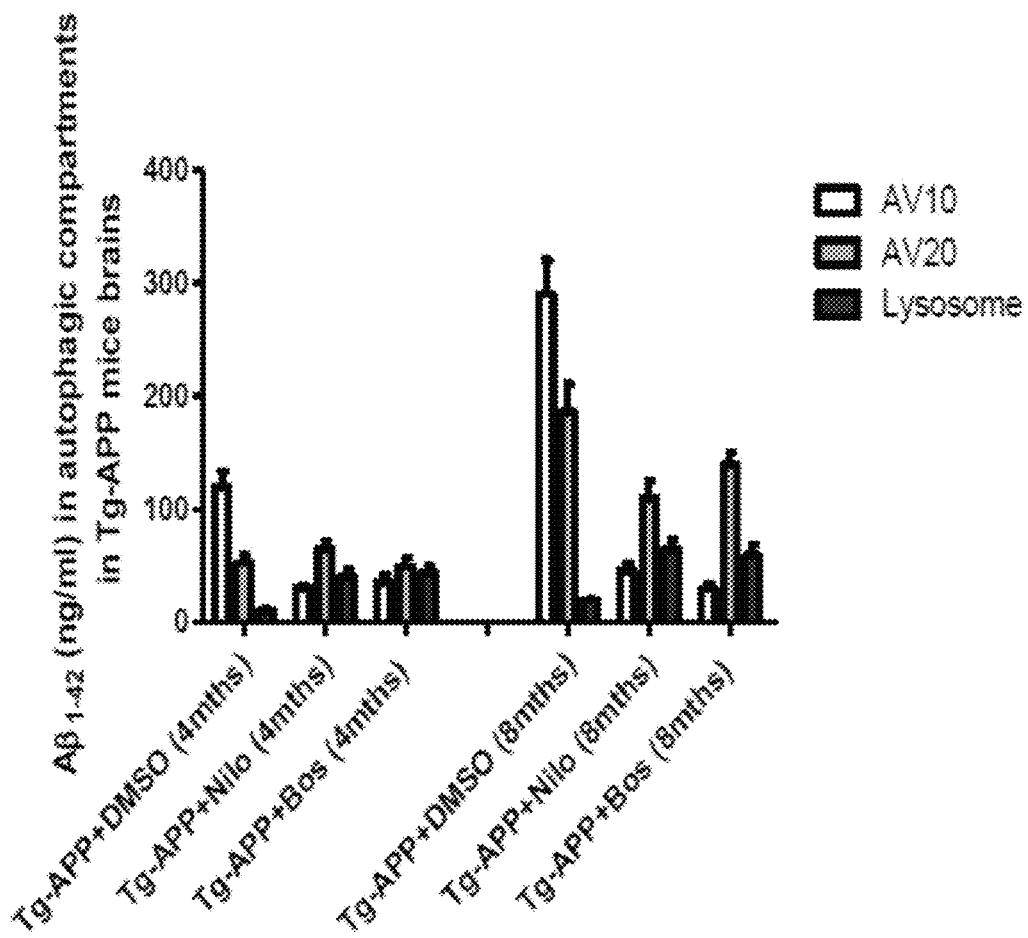

FIG. 11 is a bar graph showing that $A\beta_{1-42}$ accumulates in AV-10 in Tg-APP animals but drug treatment enhances autophagic clearance via deposition of $A\beta_{1-42}$ in AV-20 and lysosome. Bars show $A\beta_{1-42}$ in subcellular fractions, including autophagic vacuole-10 (AV-10; phagophores+autophagosomes), AV-20 (autophagosomes) and lysosomes. Transgenic 3×APP mice were injected IP with 10 mg/kg Nilotinib or 5 mg/Kg Bosutinib or DMSO once a day for 3 consecutive weeks. Brain tissues were fractionated to isolate AVs and human specific ELISA was performed to determine protein contents. N=5 animals per treatment.

Figure 12:
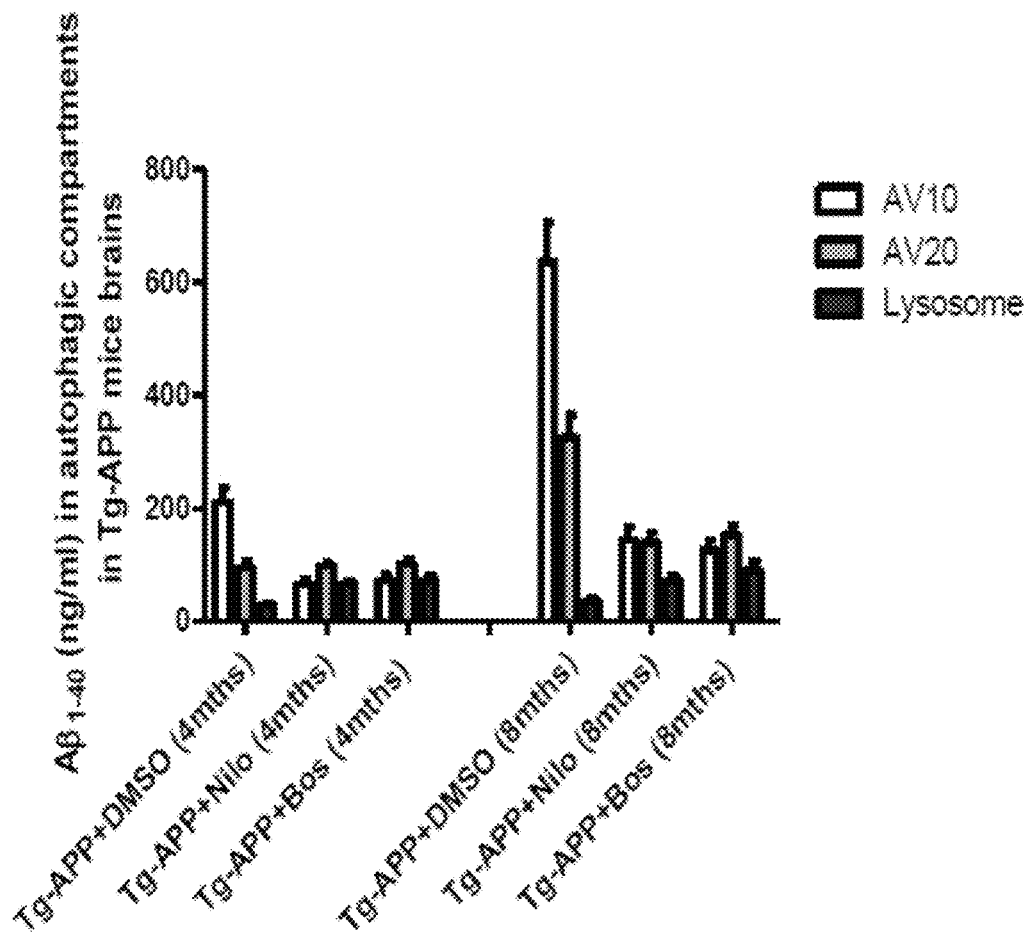

FIG. 12 is a bar graph showing that $A\beta_{1-40}$ accumulates in AV-20 in Tg-APP animals but drug treatment enhances autophagic clearance via deposition of $A\beta_{1-40}$ in AV-20 and lysosome. Histograms show $A\beta_{1-40}$ in subcellular fractions, including autophagic vacuole-10 (AV-10; phagophores+autophagosomes), AV-20 (autophagosomes) and lysosomes. Transgenic 3×APP mice were injected IP with 10 mg/kg Nilotinib or 5 mg/Kg Bosutinib or DMSO once a day for 3 consecutive weeks. Brain tissues were fractionated to isolate AVs and specific ELISA was performed to determine protein contents. N=5 animals per treatment.

Figure 13:
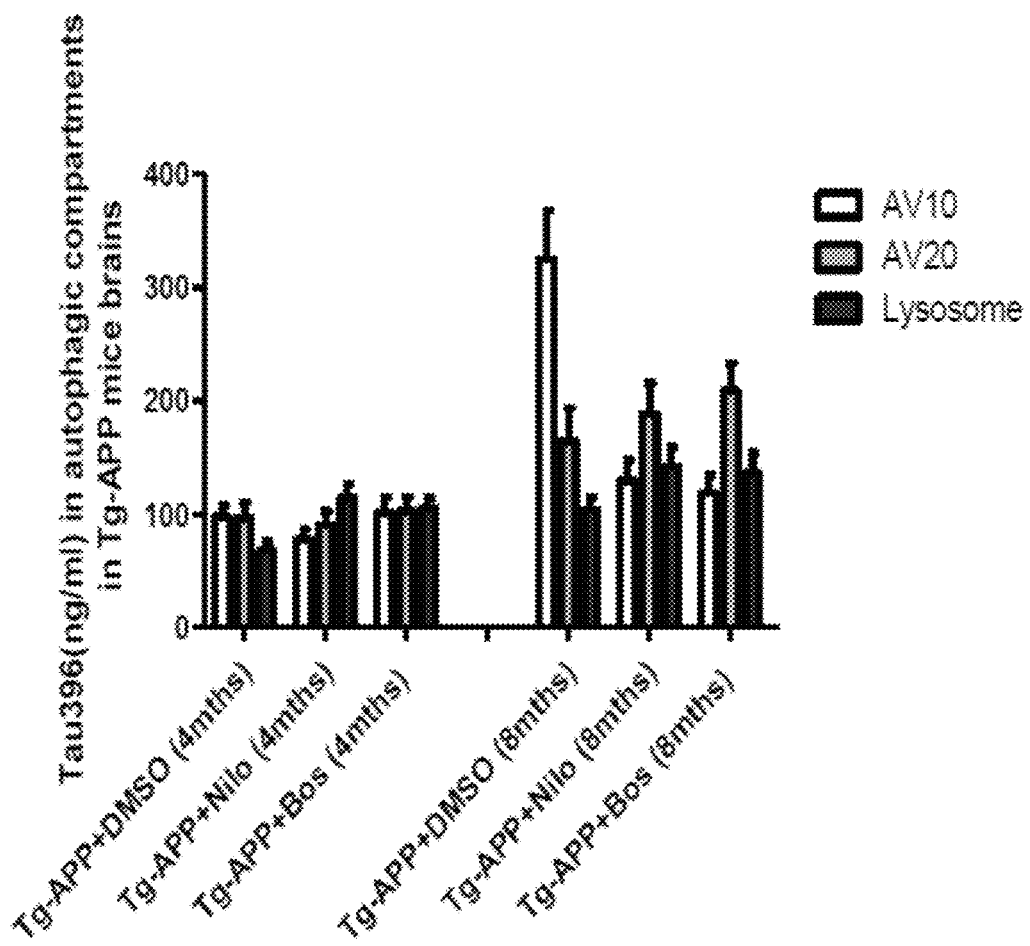

FIG. 13 is a bar graph showing that P-Tau accumulates in AV-10 in Tg-APP animals but drug treatment enhances autophagic clearance via deposition of p-Tau in AV-20 and lysosome, which contains degradative enzymes. Histograms show Tau hyper-phosphorylation (p-Tau) at serine 396 in subcellular fractions, including autophagic vacuole-10 (AV-10; phagophores+autophagosomes), AV-20 (autophagosomes) and lysosomes. Transgenic 3×APP mice were injected IP with 10 mg/kg Nilotinib or 5 mg/Kg Bosutinib or DMSO once a day for 3 consecutive weeks. Brain tissues were fractionated to isolate AVs and mouse-specific ELISA was performed to determine protein contents. N=5 animals per treatment.

Figure 14:
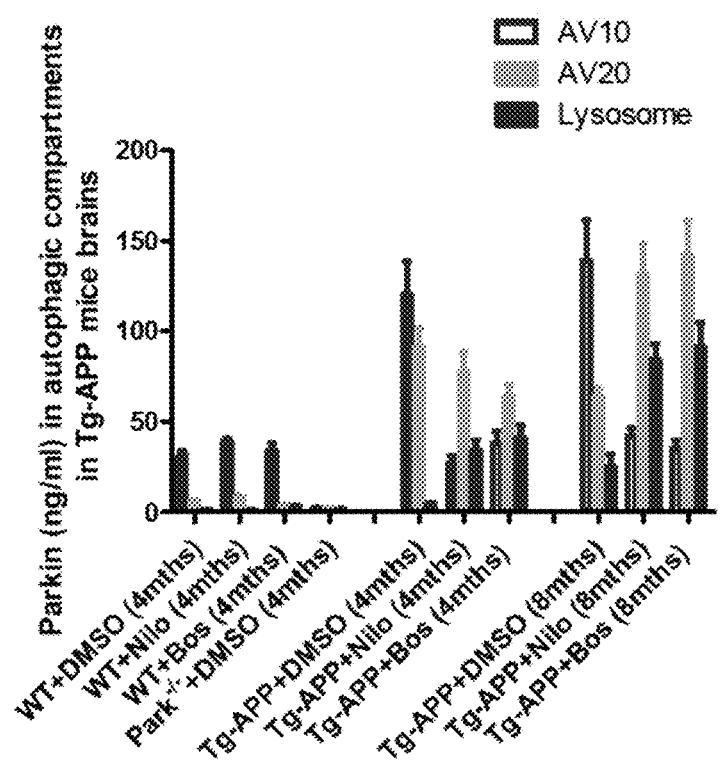

FIG. 14 is a bar graph showing that drug treatment increases parkin activity leading to protein clearance including parkin itself. Histograms show parkin in subcellular fractions, including autophagic vacuole-10 (AV-10; phagophores+autophagosomes), AV-20 (autophagosomes) and lysosomes. Transgenic 3×APP mice were injected IP with 10 mg/kg Nilotinib or 5 mg/kg Bosutinib or DMSO once a day for 3 consecutive weeks. Brain tissues were fractionated to isolate AVs and mouse specific ELISA was performed to determine protein contents. parkin accumulates in AV-10 in Tg-APP animals but drug treatment enhances autophagic clearance via deposition of parkin in AV-20 and lysosome, which contains degradative enzymes. N=5 animals per treatment.

Figure 15:
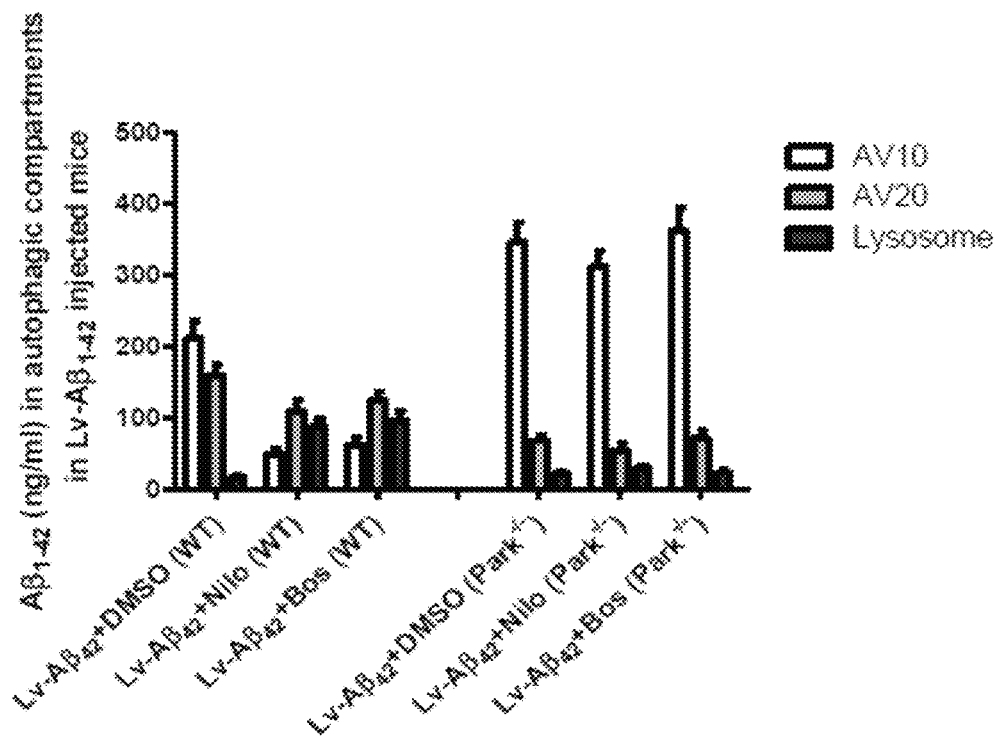

FIG. 15 is a bar graph showing that autophagic clearance is parkin-dependent. Histograms show $A\beta_{1-42}$ in subcellular fractions, including autophagic vacuole-10 (AV-10; phagophores+autophagosomes), AV-20 (autophagosomes) and lysosomes. Wild type or parkin−/− mice injected with lentiviral $A\beta_{1-42}$ for 3 weeks and treated IP with 10 mg/kg Nilotinib or 5 mg/Kg Bosutinib or DMSO once a day for 3 (additional) consecutive weeks. Brain tissues were fractionated to isolate AVs and human specific ELISA was performed to determine protein contents. $A\beta_{1-42}$ accumulates in AV-10 in lentivirus injected brains but drug treatment enhances autophagic clearance via deposition of $A\beta_{1-42}$ in AV-20 and lysosome. N=5 animals per treatment.

Figure 16:
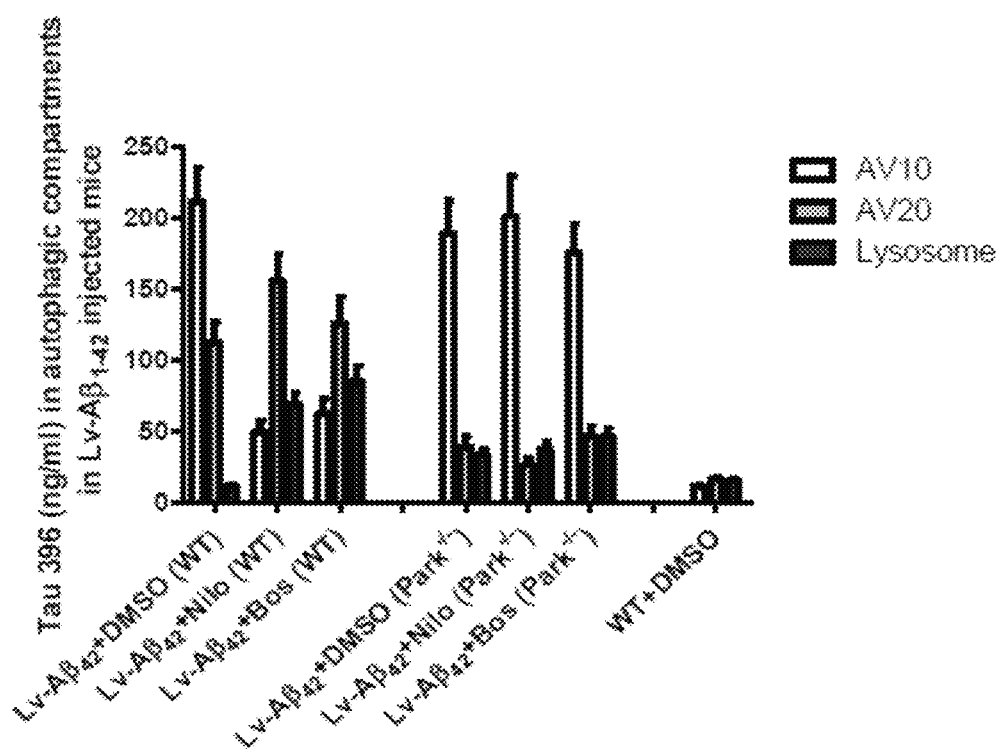

FIG. 16 is a bar graph showing that P-Tau at serine 396 accumulates in AV-10 in lentivirus injected brains but drug treatment enhances autophagic clearance via deposition of p-Tau in AV-20 and lysosome, where it is degraded. Histograms show p-Tau in subcellular fractions, including autophagic vacuole-10 (AV-10; phagophores+autophagosomes), AV-20 (autophagosomes) and lysosomes. Wild type or parkin−/− mice injected with lentiviral $A\beta_{1-42}$ for 3 weeks and treated IP with 10 mg/kg Nilotinib or 5 mg/Kg Bosutinib or DMSO once a day for 3 (additional) consecutive weeks. Brain tissues were fractionated to isolate AVs and mouse specific. ELISA was performed to determine protein contents. Autophagic clearance is parkin-dependent. N=5 animals per treatment.

Figure 17:
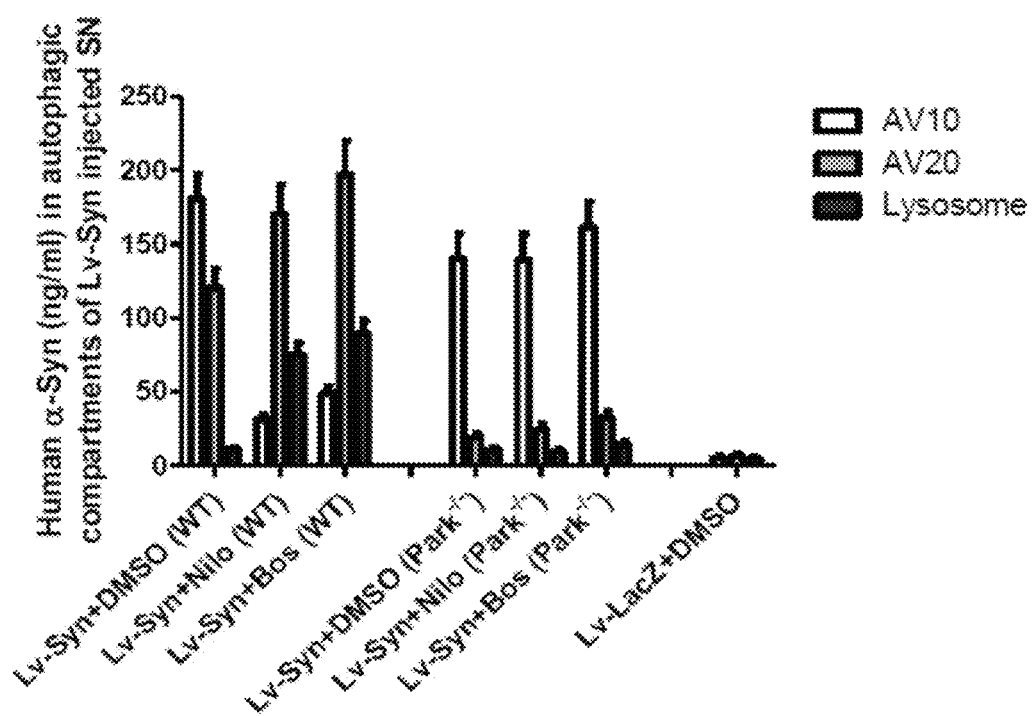

FIG. 17 is a bar graph showing that α-synuclein accumulates in AV-10 in lentivirus injected brains but drug treatment enhances autophagic clearance via deposition of α-synuclein in AV-20 and lysosome, which contains degradative enzymes. Histograms show α-synuclein in subcellular fractions, including autophagic vacuole-10 (AV-10; phagophores+autophagosomes), AV-20 (autophagosomes) and lysosomes. Wild type or parkin−/− mice injected SN with lentiviral α-synuclein for 3 weeks and treated IP with 10 mg/kg Nilotinib or 5 mg/Kg Bosutinib or DMSO once a day for 3 (additional) consecutive weeks. SN tissues were fractionated to isolate AVs and human specific ELISA was performed to determine protein contents. Autophagic clearance is parkin-dependent. N=5 animals per treatment.

Figure 18:
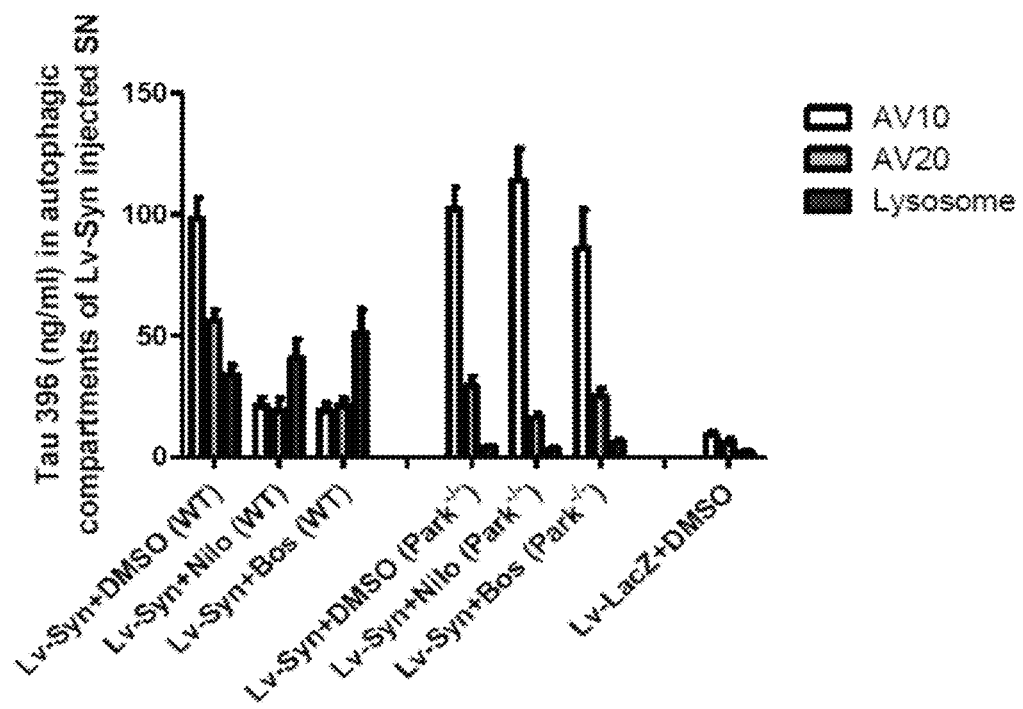

FIG. 18 is a bar graph showing that P-Tau accumulates in AV-10 in lentivirus injected brains but drug treatment enhances autophagic clearance via p-Tau deposition in AV-20 and lysosome, which contains degradative enzymes. Histograms show p-Tau at serine 396 in subcellular fractions, including autophagic vacuole-10 (AV-10; phagophores+autophagosomes), AV-20 (autophagosomes) and lysosomes. Wild type or parkin−/− mice injected SN with lentiviral α-synuclein for 3 weeks and treated IP with 10 mg/kg Nilotinib or 5 mg/Kg Bosutinib or DMSO once a day for 3 (additional) consecutive weeks. SN tissues were fractionated to isolate AVs and mouse specific ELISA was performed to determine protein contents. Autophagic clearance is parkin-dependent. N=5 animals per treatment.

Figure 19:
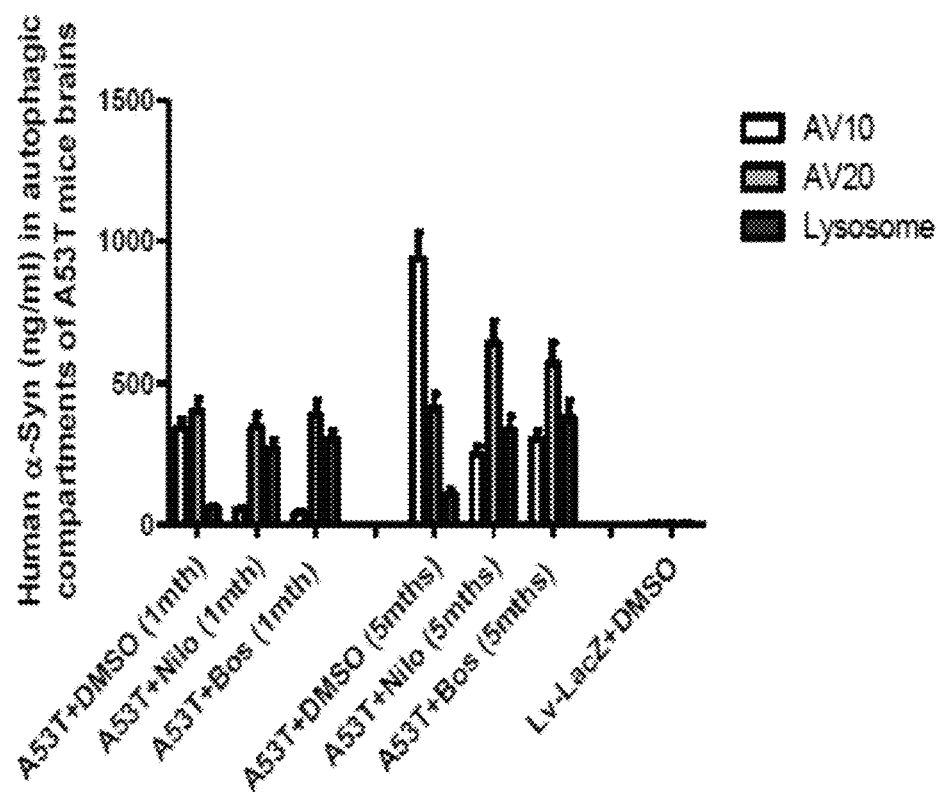

FIG. 19 is a bar graph showing that α-synuclein accumulates in AV-10 in A53T brains but drug treatment enhances autophagic clearance via α-synuclein deposition in AV-20 and lysosome. Bars show α-synuclein in subcellular fractions, including autophagic vacuole-10 (AV-10; phagophores+autophagosomes), AV-20 (autophagosomes) and lysosomes, containing digestive enzymes. Transgenic A53T mice were injected IP with 10 mg/kg Nilotinib or 5 mg/Kg Bosutinib or DMSO once a day for 3 consecutive weeks. Brain tissues were fractionated to isolate AVs and human specific ELISA was performed to determine protein contents. N=5 animals per treatment.

Figure 20:
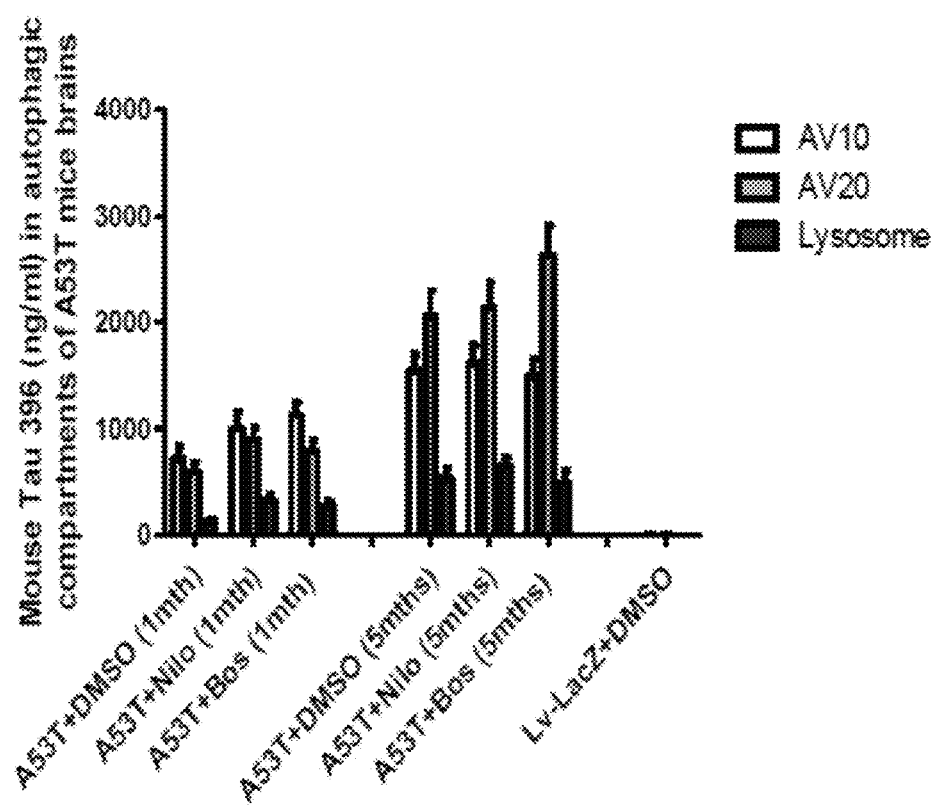

FIG. 20 is a bar graph showing that P-Tau accumulates in AV-10 in A53T brains but drug treatment enhances autophagic clearance via p-tau deposition in AV-20 and lysosome. Histograms show p-Tau at Serine 396 in subcellular fractions, including autophagic vacuole-10 (AV-10; phagophores+autophagosomes), AV-20 (autophagosomes) and lysosomes, containing digestive enzymes. Transgenic A53T mice were injected IP with 10 mg/kg Nilotinib or 5 mg/Kg Bosutinib or DMSO once a day for 3 consecutive weeks. Brain tissues were fractionated to isolate AVs and mouse specific ELISA was performed to determine protein contents. N=5 animals per treatment.

Figure 21:
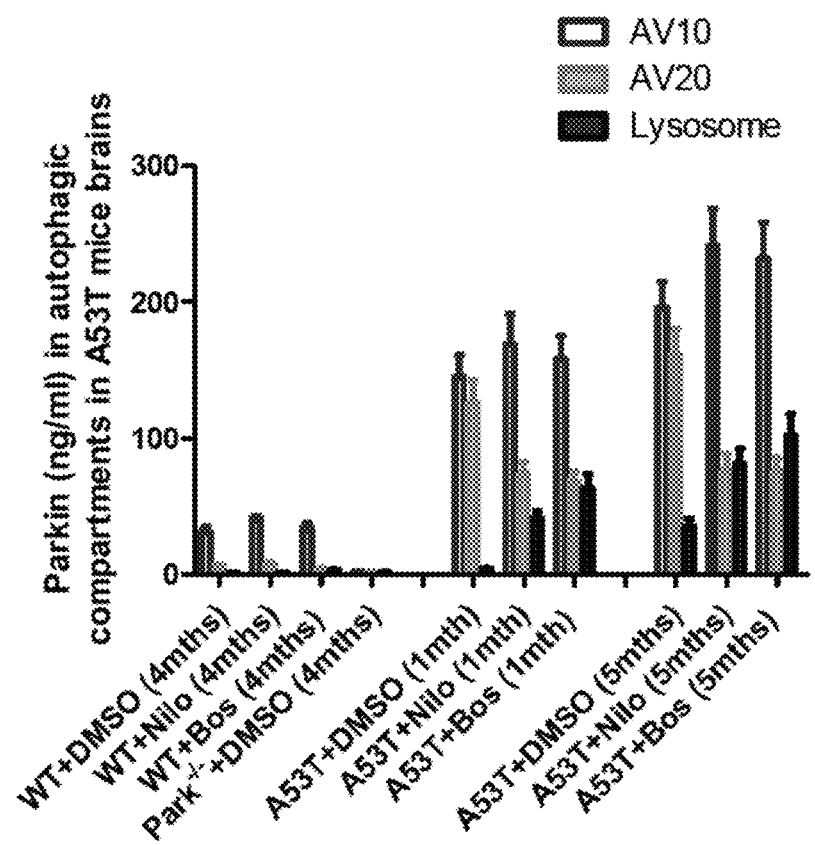

FIG. 21 is a bar graph showing that parkin accumulates in AV-10 in A53T brains but drug treatment enhances autophagic clearance via parkin deposition in AV-20 and lysosome. Bars show parkin in subcellular fractions, including autophagic vacuole-10 (AV-10; phagophores+autophagosomes), AV-20 (autophagosomes) and lysosomes, containing digestive enzymes. Transgenic A53T mice were injected IP with 10 mg/kg Nilotinib or 5 mg/Kg Bosutinib or DMSO once a day for 3 consecutive weeks. Brain tissues were fractionated to isolate AVs and mouse specific ELISA was performed to determine protein contents. N=5 animals per treatment.

Figure 22:
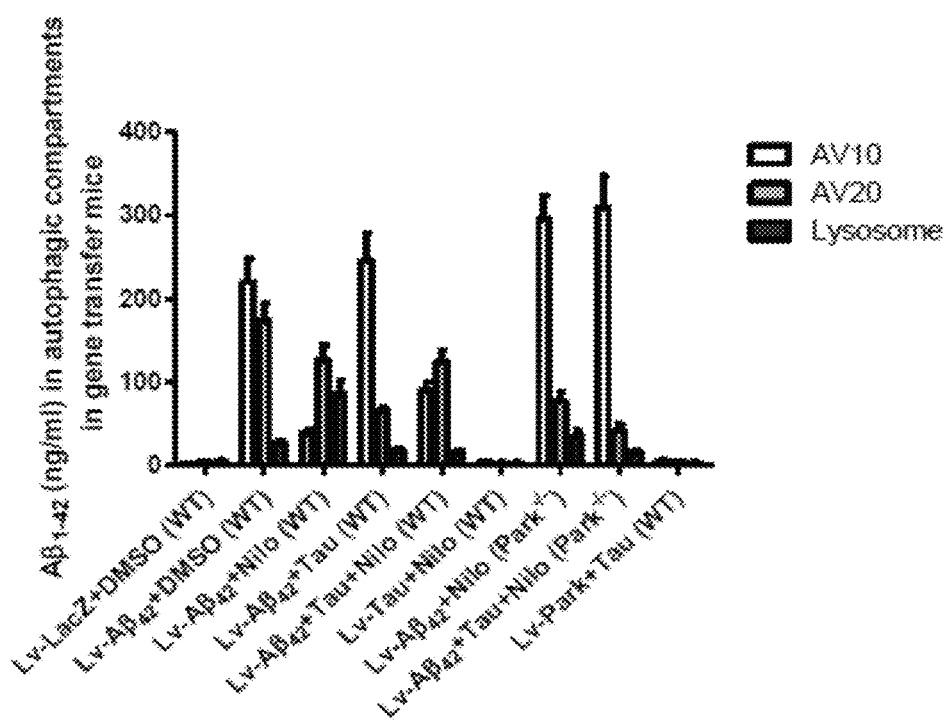

FIG. 22 is a bar graph showing that Tau expression leads to $A\beta_{1-42}$ accumulation in AV10 and AV20, but not in lysosomes, indicating decreased fusion between autophagosomes and lysosomes. Bars show $A\beta_{1-42}$ in subcellular fractions, including autophagic vacuole-10 (AV-10; phagophores+autophagosomes), AV-20 (autophagosomes) and lysosomes. Wild type or parkin−/− mice injected with lentiviral Tau±$A\beta_{1-42}$ for 3 weeks and treated IP with 10 mg/kg Nilotinib or DMSO once a day for 3 (additional) consecutive weeks. Brain tissues were fractionated to isolate AVs and human specific ELISA was performed to determine $A\beta_{1-42}$ contents. $A\beta_{1-42}$ accumulates in AV-10 in lentivirus injected brains but drug treatment enhances autophagic clearance via deposition of $A\beta_{1-42}$ in AV-20 and lysosome. Autophagic clearance is parkin-dependent. N=5 animals per treatment.

Figure 23:
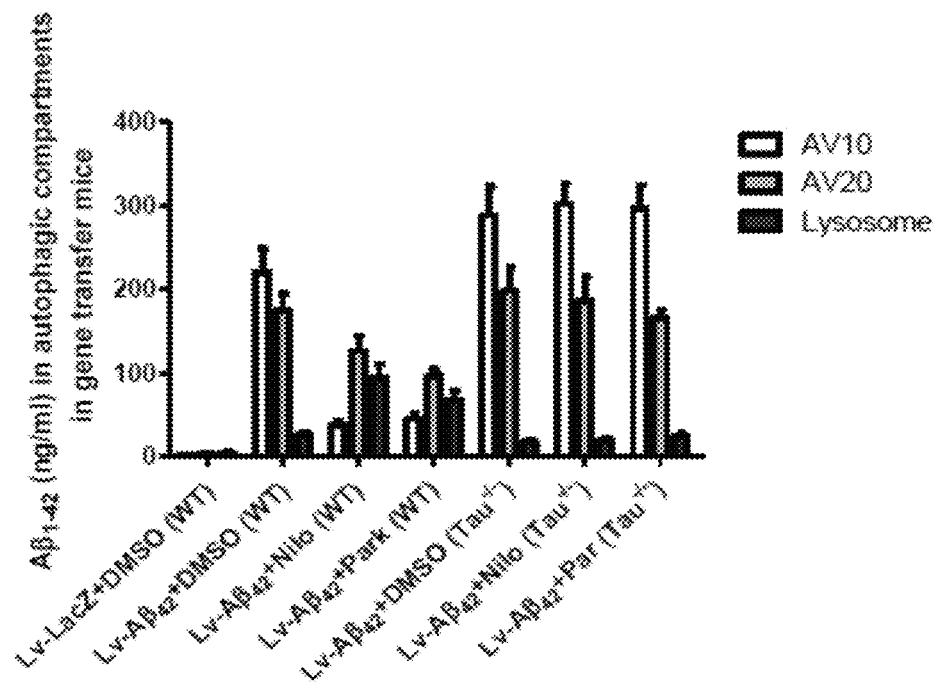

FIG. 23 is a bar graph showing that $A\beta_{1-42}$ accumulates in AV-10 in lentivirus injected brains but drug treatment enhances autophagic clearance via deposition of $A\beta_{1-42}$ in AV-20 and lysosome. Autophagic clearance is less efficient in Tau null animals with $A\beta_{1-42}$ accumulation in AV-10 and AV-20. Bars show $A\beta_{1-42}$ in subcellular fractions, including autophagic vacuole-10 (AV-10; phagophores+autophagosomes), AV-20 (autophagosomes) and lysosomes. Wild type or Tau−/− mice injected with lentiviral $A\beta_{1-42}$ for 3 weeks and treated IP with 10 mg/kg Nilotinib or 5 mg/Kg Bosutinib or DMSO once a day for 3 (additional) consecutive weeks. Brain tissues were fractionated to isolate AVs and human specific ELISA was performed to determine protein contents. N=5 animals per treatment.

Figure 24:
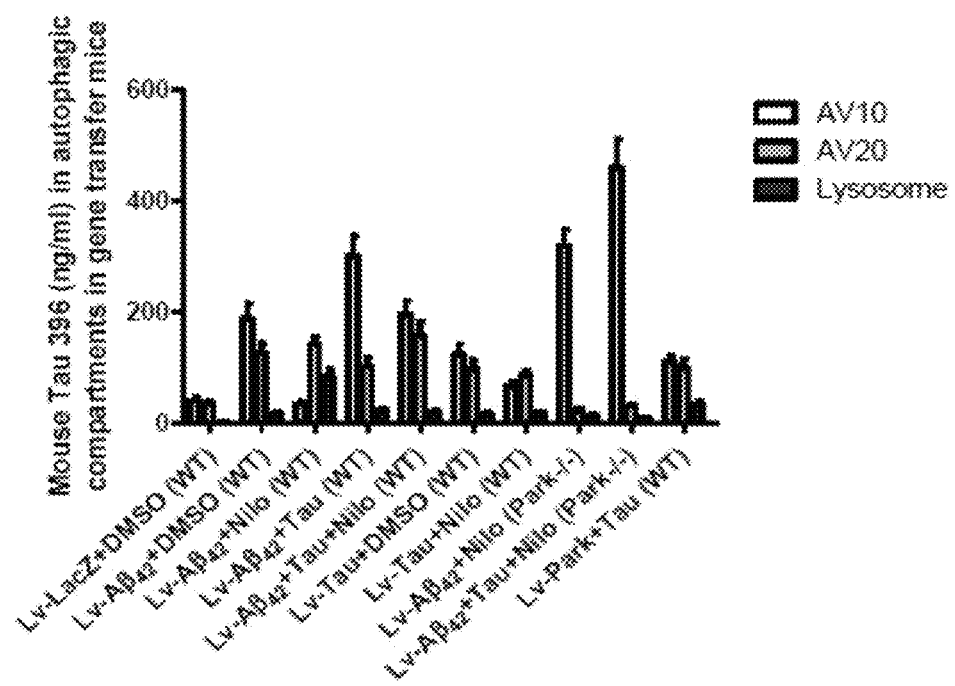

FIG. 24 is a bar graph showing that P-Tau at serine 396 accumulates in AV-10 in lentivirus injected brains but drug treatment enhances autophagic clearance via deposition of p-Tau in AV-20 and lysosome, where it is degraded. Bars show p-Tau in subcellular fractions, including autophagic vacuole-10 (AV-10; phagophores+autophagosomes), AV-20 (autophagosomes) and lysosomes. Wild type or parkin−/− mice injected with lentiviral human Tau±$A\beta_{1-42}$ for 3 weeks and treated IP with 10 mg/kg Nilotinib or 30 µL DMSO once a day for 3 (additional) consecutive weeks. Brain tissues were fractionated to isolate AVs and mouse specific ELISA was performed to determine protein contents. Autophagic clearance is parkin-dependent. N=5 animals per treatment.

Figure 25:
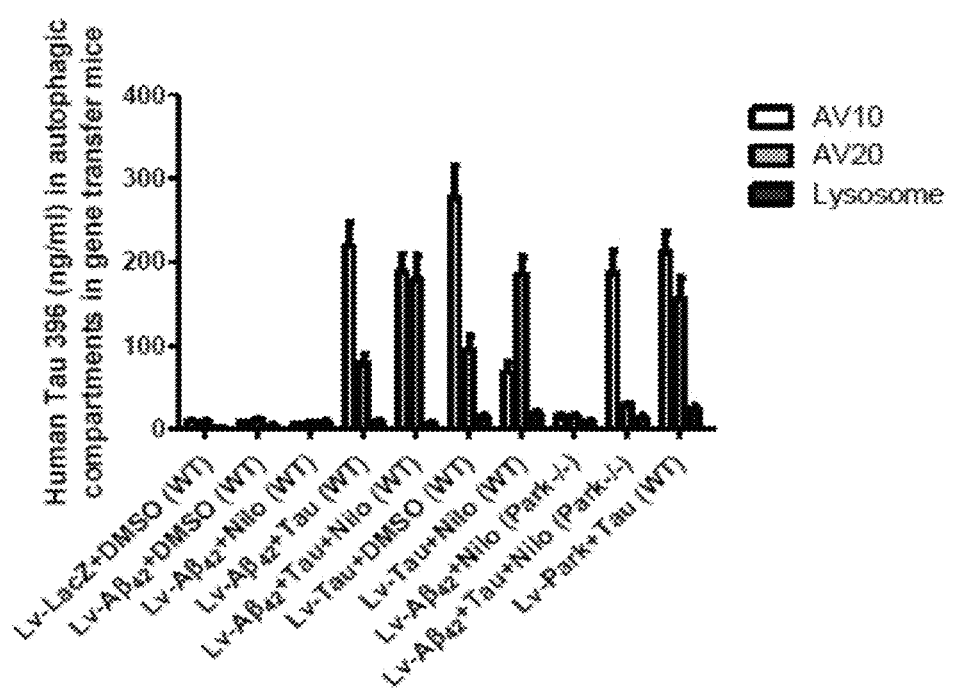

FIG. 25 is a bar graph showing that P-Tau at serine 396 accumulates in AV-10 in lentivirus injected brains but drug treatment enhances autophagic clearance via deposition of p-Tau in AV-20 and lysosome, where it is degraded. Histograms show p-Tau in subcellular fractions, including autophagic vacuole-10 (AV-10; phagophores+autophagosomes), AV-20 (autophagosomes) and lysosomes. Wild type or parkin−/− mice injected with lentiviral Tau±$A\beta_{1-42}$ for 3 weeks and treated IP with 10 mg/kg Nilotinib or 5 mg/Kg Bosutinib or DMSO once a day for 3 (additional) consecutive weeks. Brain tissues were fractionated to isolate AVs and human specific ELISA was performed to determine protein contents. Autophagic clearance is parkin-dependent. N=5 animals per treatment.

Figure 26:
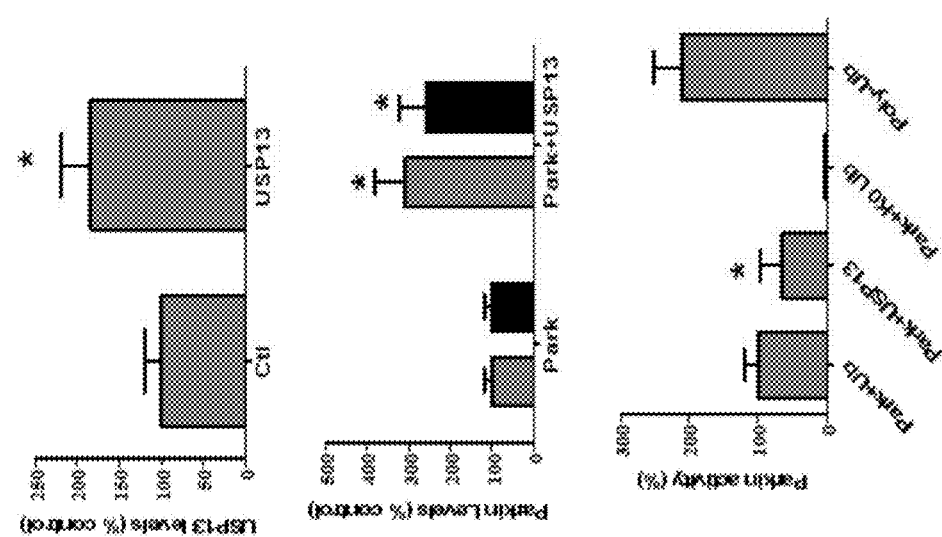
Figure 26:
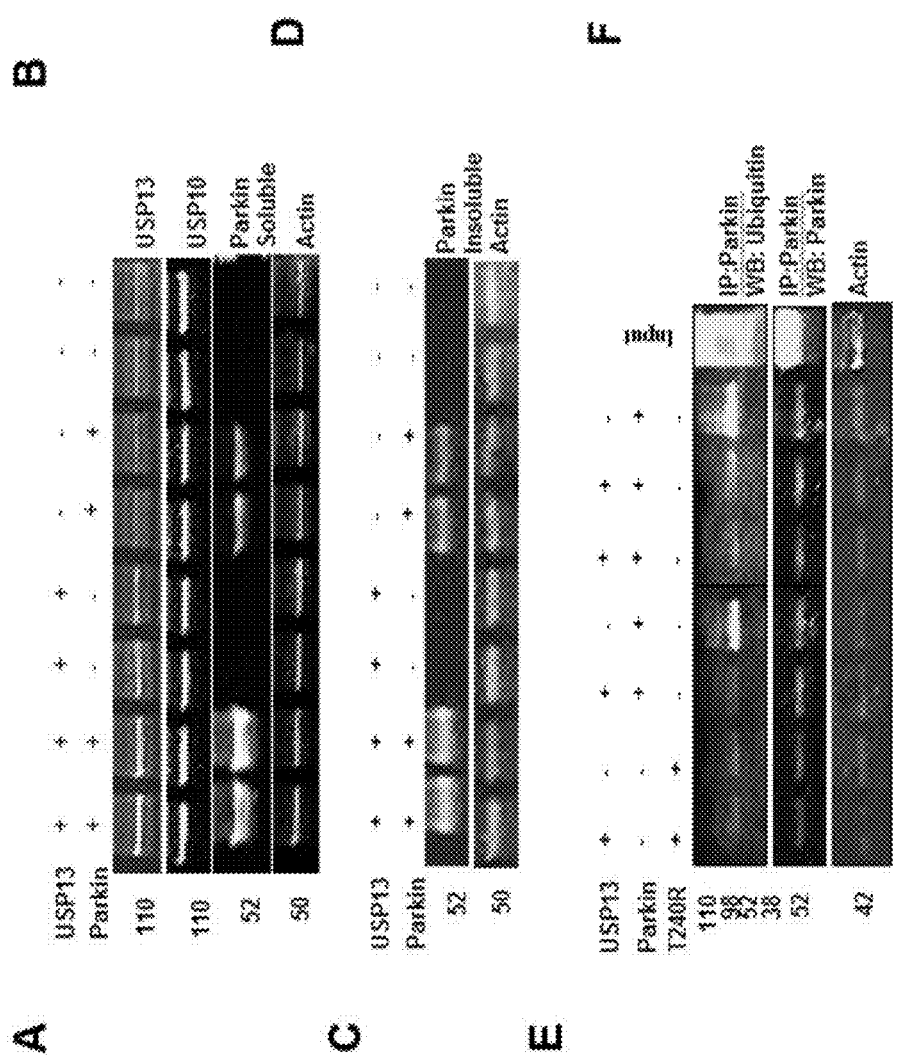

FIG. 26 is a Western blot analysis of sodium Tris EDTA NP40 (STEN) (soluble) extracts of human M17 cells. Lentiviral USP13 expression (FIG. 26A) ($1^{st}$ blot), endogenous USP10 levels (FIG. 26A) ($2^{nd}$ blot), and lentiviral parkin expression (FIG. 26A) ($3^{rd}$ blot) relative to actin (FIG. 26A) ($4^{th}$ blot) on 10% NuPAGE SDS gel are shown. FIG. 26B shows densitometry results. Western blot analysis of 4 M urea (insoluble) extracts showing parkin levels (FIG. 26C) ($1^{st}$ blot) relative to actin on 10% NuPAGE SDS gel are provided with densitometry results (FIG. 26D). FIG. 26E is a Western blot showing immunoprecipitated (IP) parkin from human M17 cells overexpressing parkin ±USP13 and probed with ubiquitin ($1^{st}$ blot), USP13 ($2^{nd}$ blot) and parkin ($3^{rd}$ blot) relative to actin and input. The graph in FIG. 26F represents parkin activity in human M17 cells as measured by ELISA in the presence of E1-E2 and ATP. N=7 for every treatment; * indicates significantly different, ANOVA, Neuman Keuls multiple comparison, P<0.05.

Figure 27:
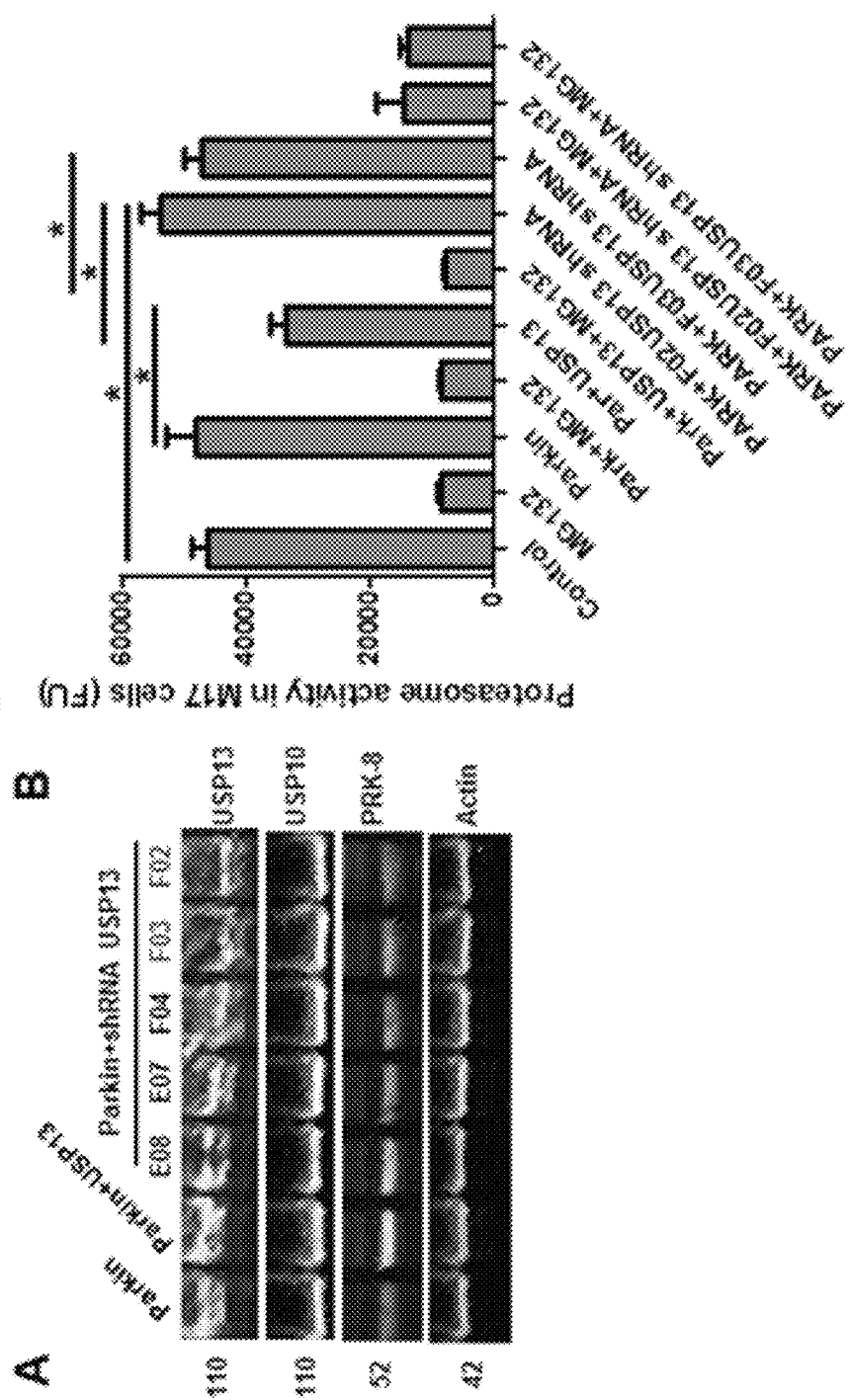

FIG. 27 is a Western blot analysis of STEN (soluble) extracts of M17 cells. FIG. 27A shows lentiviral USP13 expression ($1^{st}$ blot) and USP13 shRNA named (E08, E07, F04, F03 and F02), endogenous USP10 levels ($2^{nd}$ blot), and parkin expression ($3^{rd}$ blot) relative to actin ($4^{th}$ blot) on a 10% NuPAGE SDS gel. FIG. 27B is a graph representing chymotrypsin-like 26S proteasome activity with lentiviral parkin, USP13 or shRNA. N=4 for every treatment; *indicates significantly different, ANOVA, Neuman Keuls multiple comparison, P<0.05.

Figure 28:
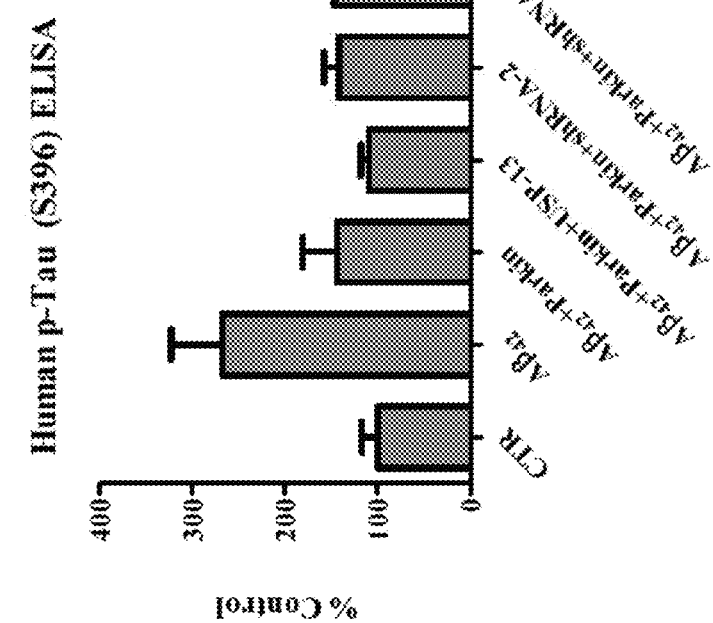
Figure 28:
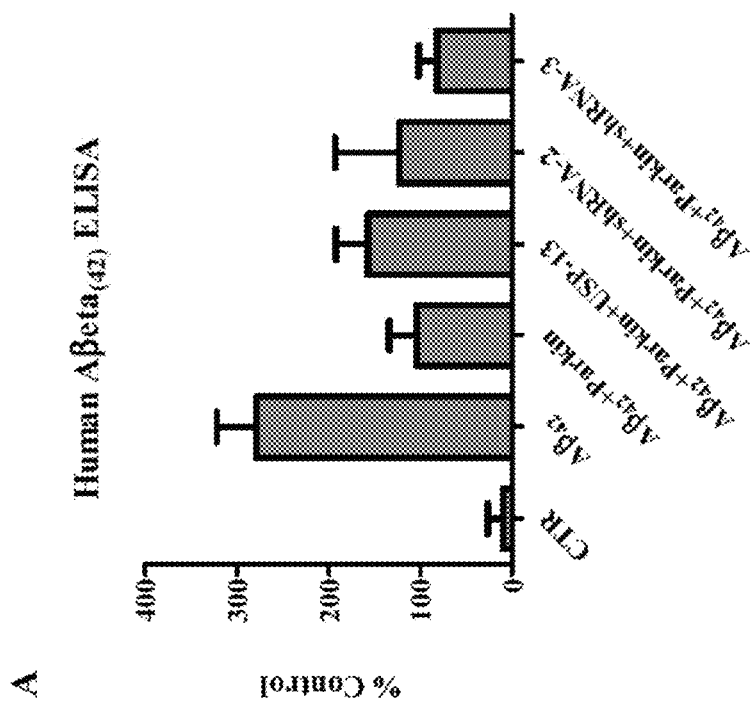
Figure 28:
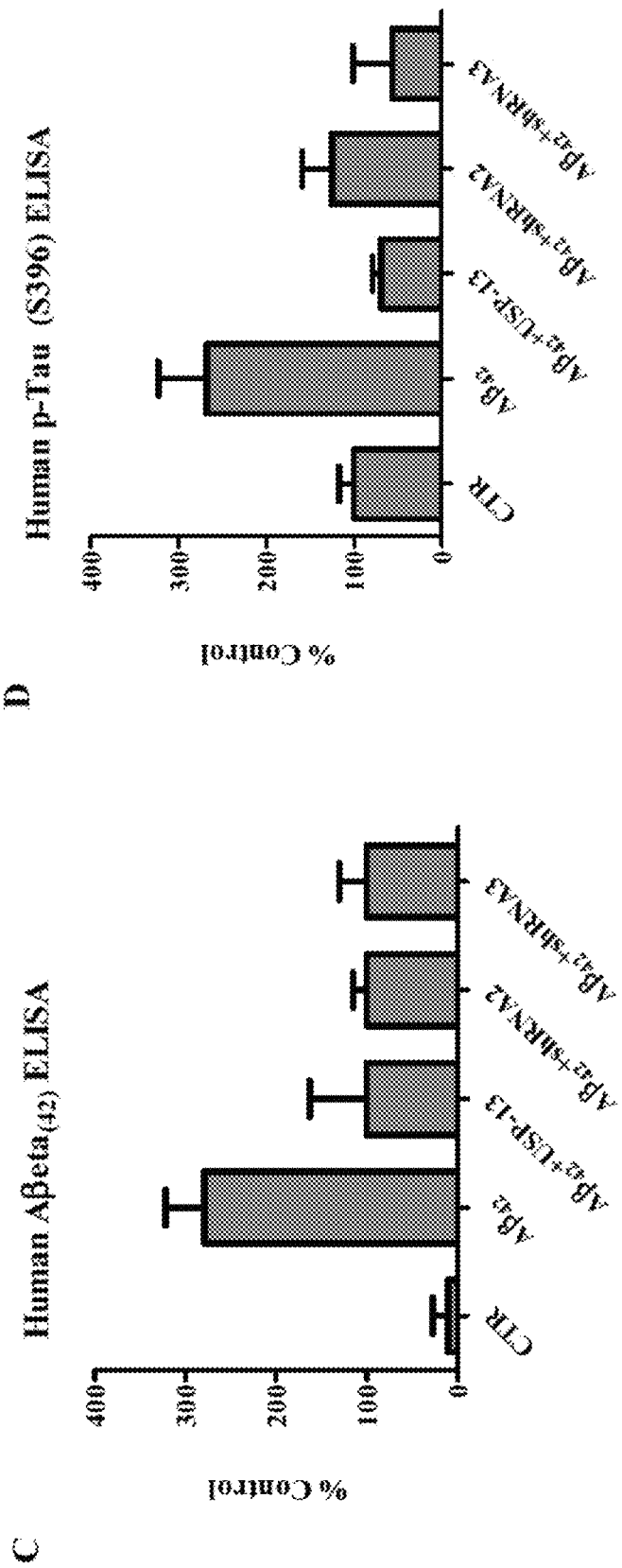

FIG. 28 shows that USP13 deletion increases parkin-mediated amyloid clearance. Human M17 cells were transfected with USP13 cDNAs and shRNAs in the presence of $\alpha\beta 42$. ELISA was performed showing the level of $\alpha\beta 42$ and hyper-phosphorylated Tau at Ser 396 in the presence of parkin (FIGS. 28A and B) and in the absence of parkin (FIGS. 28C and D) absence of parkin.

Figure 29:
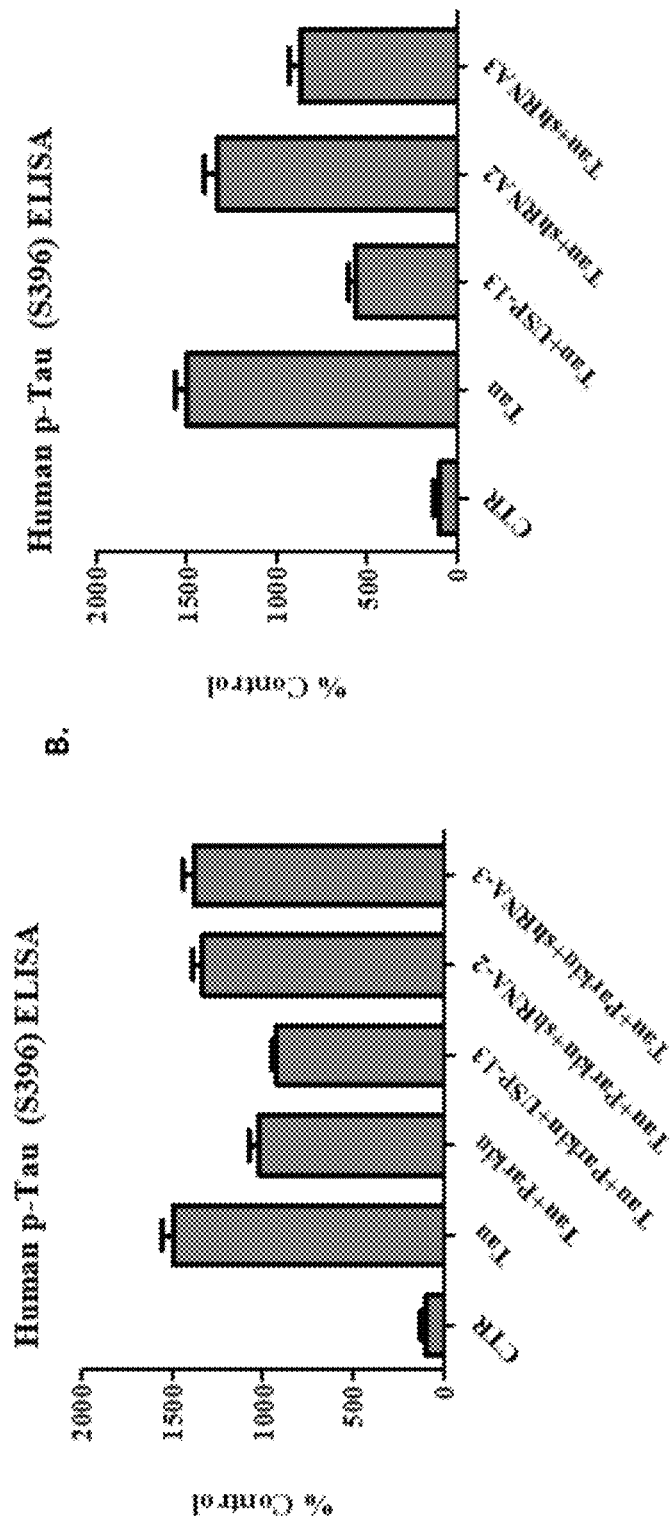

FIG. 29 shows that USP13 deletion can increase parkin-mediated Tau clearance. Human M17 cells were transfected with USP13 cDNAs and shRNAs in the presence of Tau and ELISA was performed showing the level of hyper-phosphorylated Tau at Ser 396 in the presence of parkin (FIG. 29A) and in the absence of parkin (FIG. 29B).

Figure 30:
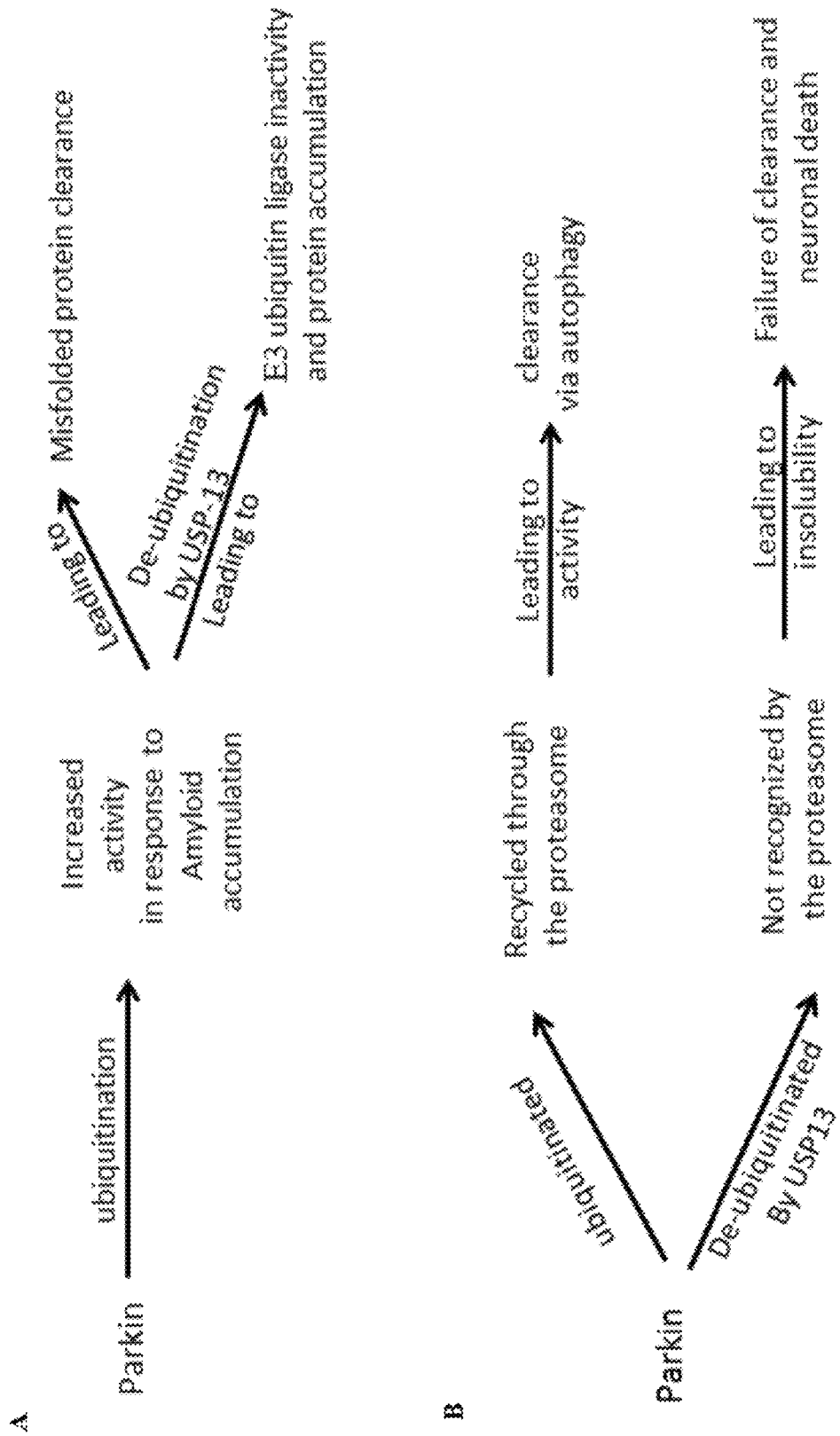

FIG. 30 shows that ubiquitinated parkin is activated in response to amyloid (alpha-Synuclein, beta-amyloid, Tau and TDP-43) accumulation, leading to facilitation of clearance. An increase in USP13 leads to parkin deubiquitination and decreased activity, resulting in misfolded protein accumulation in neurodegenerative diseases (FIG. 30A). It is likely that ubiquitination activates parkin, which is then recycled through the proteasome to prevent its accumulation (FIG. 30B). Activated parkin facilitates autophagic clearance. An increase in USP13 leads to parkin deubiquitination and decreased proteasomal recognition, leading to its instability/insolubility and accumulation. This results in subsequent autophagic failure and death of neurons (FIG. 30B).

DETAILED DESCRIPTION

Provided herein is a method of promoting parkin activity in a subject, comprising selecting a subject with a disorder associated with decreased Parkin activity and administering to the subject an effective amount of a composition that increases parkin activity, wherein the composition is an inhibitor of a deubiquitinating enzyme. A disorder associated with decreased parkin activity can be, but is not limited to, a neurodegenerative disease, a myodegenerative disease, prion disease or cancer. In the methods provided herein, neurodegenerative diseases of the central nervous system include, but are not limited to, Amyotrophic Lateral Sclerosis, Alzheimer's Disease, Parkinson's Disease, frontotemporal dementia, Huntington's Disease, Mild Cognitive Impairment, an α-Synucleinopathy, a Tauopathy or a pathology associated with intracellular accumulation of TDP-43.

In the methods provided herein, myodegenerative diseases include, but are not limited to, inclusion body myositis (IBM), spinal-bulbar muscular atrophy (SBMA), and motor neuron disease (MND). In the methods provided herein, prion diseases or transmissible spongiform encephalopathies (TSEs) include, but are not limited to, Creutzfeldt-Jakob Disease (CJD), Variant Creutzfeldt-Jakob Disease (vCJD), Gerstmann-Straussler-Scheinker Syndrome, Fatal Familial Insomnia and Kuru in humans. Animal prion diseases include, but are not limited to, Scrapie, Bovine Spongiform Encephalopathy (BSE), Chronic Wasting Disease (CWD), Transmissible mink encephalopathy, Feline spongiform encephalopathy and Ungulate spongiform encephalopathy.

As used throughout, cancer refers to any cellular disorder in which the cells proliferate more rapidly than normal tissue growth. A proliferative disorder includes, but is not limited to, neoplasms, which are also referred to as tumors. A neoplasm can include, but is not limited to, pancreatic cancer, breast cancer, brain cancer (e.g., glioblastoma), lung cancer, prostate cancer, colorectal cancer, thyroid cancer, renal cancer, adrenal cancer, liver cancer, neurofibromatosis 1, and leukemia. A neoplasm can be a solid neoplasm (e.g., sarcoma or carcinoma) or a cancerous growth affecting the hematopoietic system (e.g., lymphoma or leukemia). Other proliferative disorders include, but are not limited to neurofibromatosis.

One of skill in the art would know how to select a subject with a disorder associated with decreased parkin activity. For example, and not to be limiting, one of skill in the art knows how to diagnose a subject with or at risk of developing a neurodegenerative disease. For example, one or more of the follow tests can be used genetic test (e.g., identification of a mutation in TDP-43 gene) or familial analysis (e.g., family history), central nervous system imaging (e.g., magnetic resonance imaging and positron emission tomography), clinical or behavioral tests (e.g., assessments of muscle weakness, tremor, or memory), laboratory tests.

One of skill in the art would also know how to identify a subject with decreased parkin activity. Methods for measuring parkin activity are known in the art. See, for example, Schlossmacher and Shimura ("Parkinson's disease: assays for the ubiquitin ligase activity of neural Parkin," *Methods Mol. Biol.* 301: 351-69 (2005)); Morrison et al. ("A simple cell based assay to measure Parkin activity," *J. Neurochem.* 116(3): 342-9 (2011)) and Burns et al. (*Hum. Mol. Genet.* 18 3206-3216 (2009)).

One or more inhibitors of deubiquitinating enzymes (DUBs) can be used to increase parkin activity. Deubiquitinizing enzymes include, but are not limited to, ubiquitin carboxyl-terminal hydrolase 10 (USP10) and ubiquitin carboxyl-terminal hydrolase 13 (USP13). USP10 and USP13 are enzymes that specifically cleave ubiquitin from ubiquitin-conjugated protein substrates. Protein sequences for USP10 are provided herein as SEQ ID NO: 6 and SEQ ID NO: 7. SEQ ID NO: 6 corresponds to the protein sequence for isoform 1 of human USP10, which can be found under GenBank Accession No. NP_001259004.1. SEQ ID NO: 7 corresponds to the protein sequence for isoform 2 of human USP10, which can be found under GenBank Accession No. NP_005144.2. Nucleic acid sequences encoding USP10 isoform 1 and USP10 isoform 2 are provided herein as SEQ ID NO: 8 (GenBank Accession No. NM_001272075.1) and SEQ ID NO: 9 (GenBank Accession No. NM_005153.2), respectively. SEQ ID NO: 10 corresponds to the protein sequence for human USP13 found under GenBank Accession No. NP_003931.2. Nucleic acid sequences encoding USP13 are provided herein as SEQ ID NO: 11 (GenBank Accession No. NM_003940.2) and SEQ ID NO: 12. The coding sequence for USP13 can comprise nucleic acids 82-2673 of SEQ ID NO: 11.

As set forth above, DUBs, such as USP10 and USP13, deubiquitinate parkin, thus reducing parkin activity. Upon reduction of parkin activity, the interaction between parkin and beclin-1 is also reduced. Therefore, inhibition of DUBs prevents deubiquitination of parkin, which leads to increased parkin activity and an increase in the interaction between parkin and beclin-1. Optionally, these inhibitors can cross the blood brain barrier.

For example, one or more inhibitors of USP10 and/or USP13 can be used in the methods set forth herein. An inhibitor can be a chemical, a small or large molecule (organic or inorganic), a drug, a protein, a peptide, a cDNA, an antibody, a morpholino, a triple helix molecule, an siRNA, a shRNA, an miRNA, an antisense RNA, a ribozyme or any other compound now known or identified in the future that inhibits at least one activity of USP10 and/or USP13, for example, deubiquitination of parkin.

For example, the inhibitor can be a compound represented by formula I:

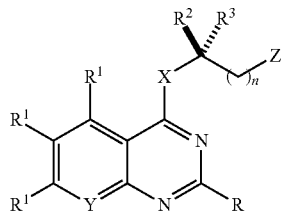

I or a pharmaceutically acceptable salt, biologically active metabolite, solvate, hydrate, prodrug, enantiomer or stereoisomer thereof, wherein n is 0, 1, 2, 3 or 4;

Y is —C($R^1$)= or —N=;

R is —H, lower alkyl, —CH3, lower fluoroalkyl, —$CH_2$F, —$CHF_2$, —$CF_3$, —$NO_2$, —OH, —$NH_2$, NH(lower alkyl), —N(lower alkyl)$_2$, or lower alkynyl;

$R^1$ is independently selected for each occurrence from the group consisting of —H, —F, —Cl, —Br, —I, —$NO_2$, —OH, —$NH_2$, —NH(lower alkyl), —N(lower alkyl)$_2$, —$CH_3$, —$CF_3$, —C(=O)(lower alkyl), —CN, —O(lower alkyl), —O(lower fluoroalkyl), —S(=O)(lower alkyl), —S(=O)$_2$lower alkyl) and C(=O)O(lower alkyl);

$R^2$ and $R^3$ are independently selected from the group consisting of —H, lower alkyl, lower fluoroalkyl, lower alkynyl and hydroxyalkyl;

X is —O—, —S—, —N(H)—, —N(lower alkyl)-, —$CH_2$—, —$CH_2CH_2$—, —$CH_2CH_2CH_2$—, —$CH_2CH_2CH_2CH_2$—, —$CH_2CH_2CH_2CH_2CH_2$— or —$CH_2CH_2CH_2CH_2CH_2CH_2$—; and Z is phenyl, pyridyl, vinyl, morphinyl, phenanthrolinyl, naphthyl, furyl or benzo[d]thiazolyl; and optionally substituted with one or more substitutents selected from the group consisting of —CH3, lower alkyl, fluoroalkyl, —$OCH_3$, —$OCF_3$, lower fluoroalkoxy, —F, —Cl, —Br, —I, —$NO_2$, lower alkyoxy, —NH(lower alkyl), —N(lower alkyl)$_2$, —$CF_3$, and 3,4-methylene dioxy. Optionally, the compound of formula I is not

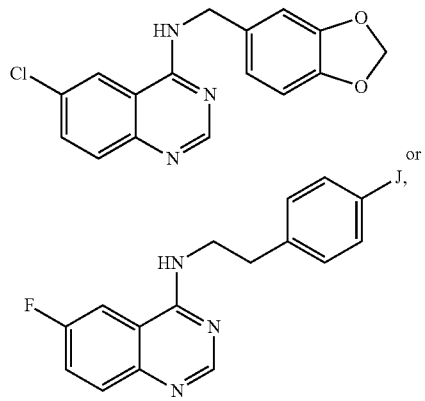

J, wherein J is Cl, $OCHF_2$, $OCH_2CH_3$, $OCH_2CF_3$, $O(CH_2)_2CH_3$, $OCH(CH_3)_2$, $O(CH_2)_3CH_3$, or O(cyclopentyl).

A non-limiting example of Formula 1 that can be used in the method set forth herein is spautin-1, or a derivative thereof. Pharmaceutical salts of spautin-1 and its derivatives are also provided herein.

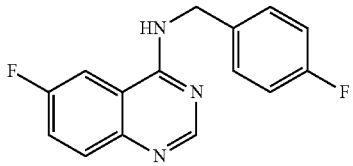

spautin-1

Identification of additional inhibitors can be determined using methods known in the art. See, for example, Lee et al. "A High-Throughput Screening Method for Identification of Inhibitors of the Deubiquitinating Enzyme USP14," *Curr. Protoc. Chem. Biol.* 4: 311-330 (2012); Tian et al. "Characterization of selective ubiquitin and ubiquitin-like protease inhibitors using a fluorescence-based multiplex assay format," *Assay Drug Dev. Technol.* 9(2): 165-173 (2011), both of which are incorporated herein in their entireties by this reference.

Other examples of inhibitors include, but are not limited to, shRNA sequences that inhibit USP13, such as, SEQ ID NOs: 1-4, set forth in the Examples. Additional examples of shRNA sequence that can be used to inhibit USP13 include, but are not limited to, SEQ ID NO: 13 (5'AAATCGTCATCAG-TATCTA3') and SEQ ID NO: 14 (5'CCATGTGAACAAT-GATCCA3'). Other antisense, siRNA or shRNA sequences can be readily obtained by one of skill in the art based on the known coding sequences of USP10 and USP13 provided herein.

The methods set forth herein optionally include administering a second therapeutic agent to the subject. For example, in order to treat a neurodegenerative disorder, the second therapeutic agent can be selected from the group consisting of levadopa, a dopamine agonist, an anticholinergic agent, a monoamine oxidase inhibitor, a COMT inhibitor, amantadine, rivastigmine, an NMDA antagonist, a cholinesterase inhibitor, riluzole, an anti-psychotic agent, an antidepressant, and tetrabenazine. In another example, in order to treat cancer, the second therapeutic agent, can be, for example, a chemotherapeutic agent or radiation.

As used throughout, an increase in parkin activity, and/or an increase in the interaction between parkin and beclin-1 in a subject can be an increase of about 10%, 20%, 30%, 40%, 50%, 60%, 70%, 80% 90%, 100% or greater as compared to a control. For example, the increase in parkin activity and/or the increase in the interaction between parkin and beclin-1 can be an increase of about 10%, 20%, 30%, 40%, 50%, 60%, 70%, 80% 90%, 100% or greater as compared to a subject that was not administered a deubiquitinating enzyme inhibitor or a control value.

The amount of inhibition or reduction of activity of the deubiquitinating enzyme does not have to be complete as this can range from a decrease to complete ablation of enzymatic activity. For example, the reduction can be about a 10, 20, 30, 40, 50, 60, 70, 80, 90, 100%, or any amount of reduction in between Inhibition or reduction of activity of the deubiquitinating enzyme can be due to a decrease in mRNA expression, a decrease in protein expression, and/or a decrease in the enzymatic activity of the deubiquitinating enzyme.

Further provided is a method of treating or preventing a neurodegenerative disease, a myodegenerative disease or prion disease in a subject, comprising: selecting a subject with a neurodegenerative disease of the central nervous system, a myodegenerative disease, a prion disease or at risk for a neurodegenerative disease of the central nervous system, a myodegenerative disease or a prion disease; and administering to the subject an effective amount of a composition that increases parkin activity, wherein the composition is an inhibitor of a deubiquitinating enzyme.

Also provided is a method of treating or preventing cancer in a subject, comprising: selecting a subject cancer or at risk for cancer; and administering to the subject an effective amount of a composition that increases parkin activity, wherein the composition is an inhibitor of a deubiquitinating enzyme.

The deubiquitinating enzyme inhibitors can be in a pharmaceutically acceptable carrier. The term carrier means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject. Such pharmaceutically acceptable carriers include sterile biocompatible pharmaceutical carriers, including, but not limited to, saline, buffered saline, artificial cerebral spinal fluid, dextrose, and water.

Modes of administration of the compositions used in the invention are exemplified below. Any of the inhibitors described herein can be delivered by any of a variety of routes including: by injection (e.g., subcutaneous, intramuscular, intravenous, intra-arterial, intraperitoneal), by continuous intravenous infusion, cutaneously, dermally, transdermally, orally (e.g., tablet, pill, liquid medicine, edible film strip), by implanted osmotic pumps, by suppository, or by aerosol spray. Routes of administration include, but are not limited to, topical, intradermal, intrathecal, intralesional, intratumoral, intrabladder, intravaginal, intra-ocular, intrarectal, intrapulmonary, intracranial, intraventricular, intraspinal, dermal, subdermal, intra-articular, placement within cavities of the body, nasal inhalation, pulmonary inhalation, impression into skin, and electroporation.

In an example in which a nucleic acid is employed, such as an antisense, shRNA, or siRNA molecule, the nucleic acid can be delivered intracellularly (for example by expression from a nucleic acid vector or by receptor-mediated mechanisms), or by an appropriate nucleic acid expression vector which is administered so that it becomes intracellular, for example by use of a retroviral vector (see U.S. Pat. No. 4,980,286), or by direct injection, or by use of microparticle bombardment (such as a gene gun; Biolistic, Dupont), or coating with lipids or cell-surface receptors or transfecting agents, or by administering it in linkage to a homeobox-like peptide which is known to enter the nucleus (for example Joliot et al., *Proc. Natl. Acad. Sci. USA* 1991, 88:1864-8). Antisense or siRNA carriers also include, polyethylene glycol (PEG), PEG-liposomes, branched carriers composed of histidine and lysine (HK polymers), chitosan-thiamine pyrophosphate carriers, surfactants, nanochitosan carriers, and D5W solution. The present disclosure includes all forms of nucleic acid delivery, including synthetic oligos, naked DNA, plasmid and viral delivery, integrated into the genome or not.

As mentioned above, vector delivery can be via a viral system, such as a retroviral vector system which can package a recombinant retroviral genome (see e.g., Pastan et al., *Proc. Natl. Acad. Sci. U.S.A.* 85:4486, 1988; Miller et al., *Mol. Cell. Biol.* 6:2895, 1986). The exact method of introducing the altered nucleic acid into mammalian cells is, of course, not limited to the use of retroviral vectors. Other techniques are widely available for this procedure including the use of adenoviral vectors (Mitani et al., *Hum. Gene Ther.* 5:941-948, 1994), adeno-associated viral (AAV) vectors (Goodman et al., *Blood* 84:1492-1500, 1994), lentiviral vectors (Naidini et al., *Science* 272:263-267, 1996), and pseudotyped retroviral vectors (Agrawal et al., *Exper. Hematol.* 24:738-747, 1996). It is also possible to deliver short hairpin RNAs (shRNAs) via vector delivery systems in order to inhibit gene expression (See Pichler et al. "In vivo RNA interference-mediated ablation of MDR1 P-glycoprotein." *Clin Cancer Res.* Jun. 15, 2005; 11(12):4487-94; Lee et al. "Specific inhibition of HIV-1 replication by short hairpin RNAs targeting human cyclin T1 without inducing apoptosis." *FEBS Lett.* Jun. 6, 2005; 579(14):3100-6.).

Physical transduction techniques can also be used, such as liposome delivery and receptor-mediated and other endocytosis mechanisms (see, for example, Schwartzenberger et al., *Blood* 87:472-478, 1996) to name a few examples. This invention can be used in conjunction with any of these or other commonly used gene transfer methods.

The effective amount of an inhibitor can depend on the nature of the disease and can be determined by standard clinical techniques. Therefore, these amounts will vary. For example, the dosage can be anywhere from 0.01 mg/kg to 100 mg/kg. Multiple dosages can also be administered depending on the disease, and the subject's condition. In addition, in vitro assays can be employed to identify optimal dosage ranges. The precise dose to be employed in the formulation will also depend on the route of administration, and the seriousness of the disease or disorder, and should be decided according to the judgment of the practitioner and each subject's circumstances. Effective doses can be extrapolated from dose-response curves derived from in vitro or animal model test systems.

The disclosure also provides a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration. Instructions for use of the composition can also be included.

Depending on the intended mode of administration, the pharmaceutical composition can be in the form of solid, semi-solid, or liquid dosage forms, such as, for example, tablets, suppositories, pills, capsules, powders, liquids, aerosols, or suspensions, preferably in unit dosage form suitable for single administration of a precise dosage. The compositions will include a therapeutically effective amount of the compound described herein or derivatives thereof in combination with a pharmaceutically acceptable carrier and, in addition, can include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005.

Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

Compositions containing one or more of the compounds described herein or pharmaceutically acceptable salts or prodrugs thereof suitable for parenteral injection can comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions can also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like can also be included. Prolonged absorption of the injectable pharmaceutical form can be brought about by the use of agents delaying absorption, for example, aluminum monostearate and gelatin.

Solid dosage forms for oral administration of the compounds described herein or pharmaceutically acceptable salts or prodrugs thereof include capsules, tablets, pills, powders, and granules. In such solid dosage forms, the compounds described herein or derivatives thereof is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms can also comprise buffering agents.

Solid compositions of a similar type can also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They can contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or pharmaceutically acceptable salts or prodrugs thereof include pharmaceutically acceptable emulsions, solutions, suspensions, syrups, and elixirs. In addition to the active compounds, the liquid dosage forms can contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, can contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or pharmaceutically acceptable salts or prodrugs thereof for rectal administrations are optionally suppositories, which can be prepared by mixing the compounds with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

As used throughout, treat, treating, and treatment refer to a method of reducing or delaying one or more effects or symptoms of a disease or disorder, for example, a neurodegenerative disease or cancer. The subject can be diagnosed with a disease or disorder. Treatment can also refer to a method of reducing the underlying pathology rather than just the symptoms. The effect of the administration to the subject can have the effect of, but is not limited to, reducing one or more symptoms of the disease or disorder, a reduction in the severity of the disease or disorder, the complete ablation of the 1 disease or disorder, or a delay in the onset or worsening of one or more symptoms. For example, a disclosed method is considered to be a treatment if there is about a 10% reduction in one or more symptoms of the disease in a subject when compared to the subject prior to treatment or when compared to a control subject or control value. Thus, the reduction can be about a 10, 20, 30, 40, 50, 60, 70, 80, 90, 100%, or any amount of reduction in between.

As utilized herein, by prevent, preventing, or prevention is meant a method of precluding, delaying, averting, obviating, forestalling, stopping, or hindering the onset, incidence, severity, or recurrence of the neurodegenerative disease or disorder. For example, the disclosed method is considered to be a prevention if there is a reduction or delay in onset, incidence, severity, or recurrence of neurodegeneration or one or more symptoms of neurodegeneration (e.g., tremor, weakness, memory loss, rigidity, spasticity, atrophy) in a subject susceptible to neurodegeneration as compared to control subjects susceptible to neurodegenration that did not receive an a deubiquitinating enzyme inhibitor that increases parkin activity. The disclosed method is also considered to be a prevention if there is a reduction or delay in onset, incidence, severity, or recurrence of neurodegeneration or one or more symptoms of neurodegeneration in a subject susceptible to neurodegeneration after receiving an agent that promotes parkin activity as compared to the subject's progression prior to receiving treatment. Thus, the reduction or delay in onset, incidence, severity, or recurrence of neurodegeneration can be about a 10, 20, 30, 40, 50, 60, 70, 80, 90, 100%, or any amount of reduction in between.

As used throughout, by subject is meant an individual. Preferably, the subject is a mammal such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, ferret, chinchilla, mouse, rabbit, rat, gerbil, guinea pig, etc.). Thus, veterinary uses and medical formulations are contemplated herein.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties. A number of embodiments have been described. Nevertheless, it will be understood that various modifications may be made. Accordingly, other embodiments are within the scope of the following claims.

Example I

Figure 1:
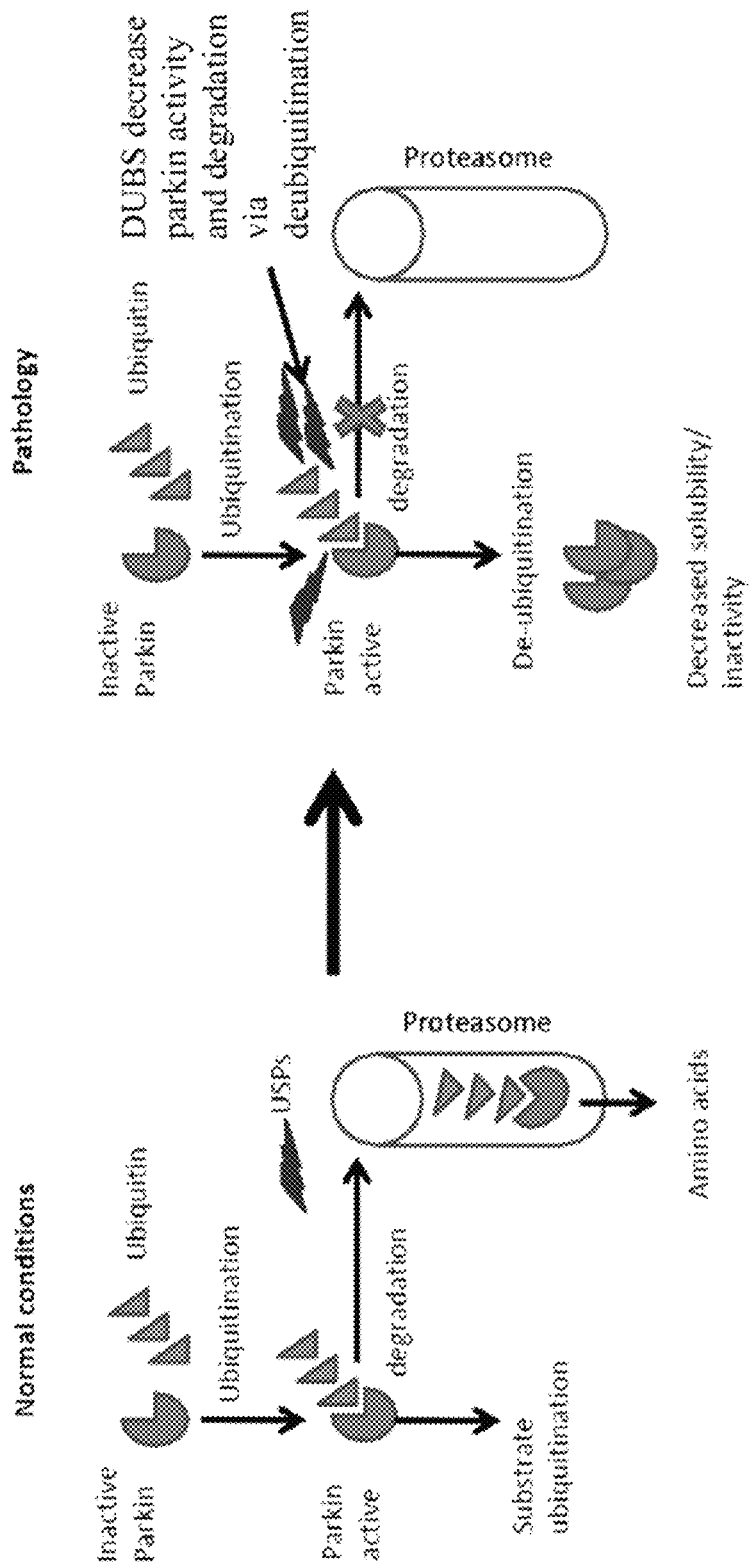
FIG. 1 is a diagram showing that parkin activity is necessary to clear misfolded proteins via autophagy and the proteasome. Under normal conditions, parkin goes from an inactive to an active state upon ubiquitination. Active parkin facilitates degradation of proteins via autophagy and the proteasome. In certain diseases, for example, a neurodegenerative disease, myodegenerative disease, prion disease or cancer, deubiquitinating enzymes decrease parkin activity, by deubiquitinating parkin, thus decreasing degradation of proteins via autophagy and the proteasome.

Parkin activity is necessary to clear misfolded proteins via autophagy and the proteasome. As set forth herein, parkin must be ubiquitinated in order to be in an active form that effects degradation of its substrates. In neurodegenerative diseases, including Alzheimer's and Parkinson's disease brains, parkin is insoluble likely due to lack of activity or lack of degradation. Parkin must be ubiquitinated to be degraded by the proteasome and must be ubiquitinated to be active. Therefore, the balance between parkin activity and re-cycling via degradation is a critical mechanism to keep parkin functioning. As shown is FIG. 1, parkin activity is necessary to clear misfolded proteins via autophagy and the proteasome. Under normal conditions, parkin goes from an inactive to an active state upon ubiquitination. Active parkin facilitates degradation of proteins via autophagy and the proteasome. In certain diseases, for example, a neurodegenerative disease, myodegenerative disease, prion disease or cancer, deubiquitinating enzymes decrease parkin activity, by deubiquitinating parkin, thus decreasing degradation of proteins via autophagy and the proteasome.

Figure 2:
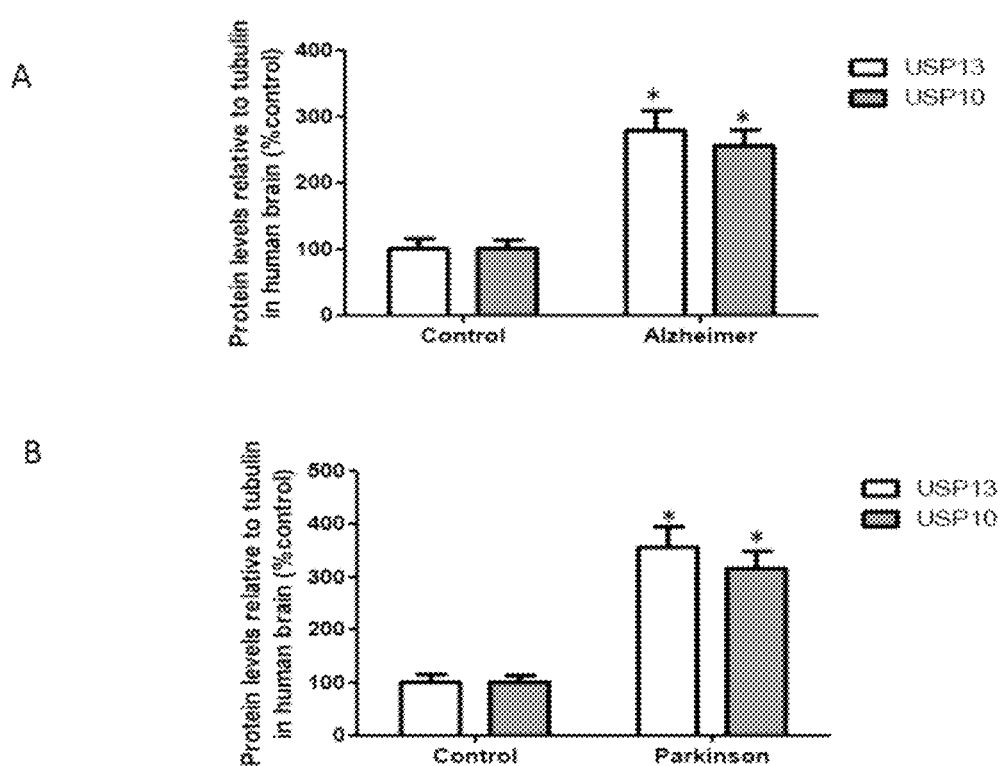
FIG. 2 shows that the level of brain deubiquitinases (USP10 and USP13) is increased in post-mortem human Alzheimer's Disease (AD) (FIG. 2A) and Parkinson's Disease (PD) (FIG. 2B) brains. Densitometry analysis of post-mortem cortex in AD (N=12) and age-matched control subjects (N=7) shows increased levels of USP10 and USP13 in AD cortex compared to control (FIG. 2A). Densitometry analysis of post-mortem caudate in PD (N=9) and age-matched control subjects (N=7) shows A) increased levels of USP10 and USP13 in PD compared to control (FIG. 2B). Mann Whitney, p<0.05. mean±SEM.
Figure 3:
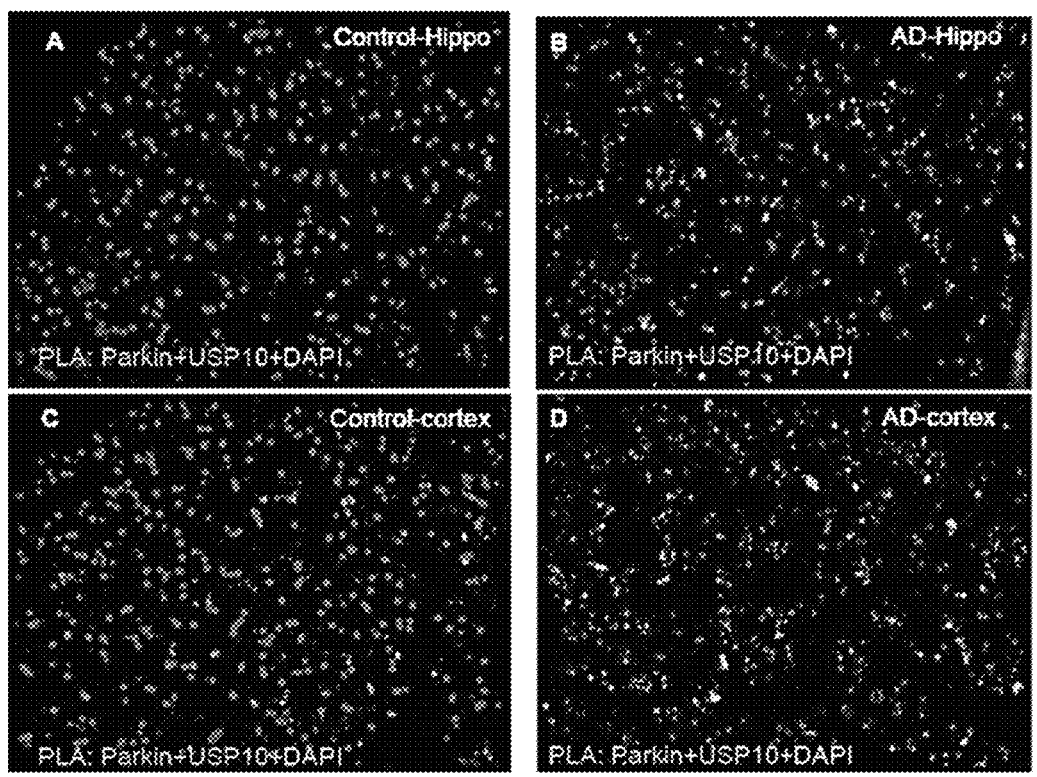
FIG. 3 shows photomicrographs of control (FIGS. 3A, 3C) and post-mortem human AD (FIGS. 3B, 3D) brains, indicating that parkin interaction with deubiquitinase (USP-10) is increased in AD. A Proximity Ligation Assay (PLA) in situ on 30 mm thick human brain sections shows parkin and ubiquitin specific peptidase 10 (USP10). The interaction between parkin and ubiquitin specific peptidase 10 (USP10) is increased in human hippocampus (Figure A and B) and cortex (Figures C and D) in AD. The increase in USP10 level is paralleled by increased interaction with parkin, indicative of parkin deubiquitination and inactivity, which leads to accumulation and decreased solubility in the human brain.
Figure 4:
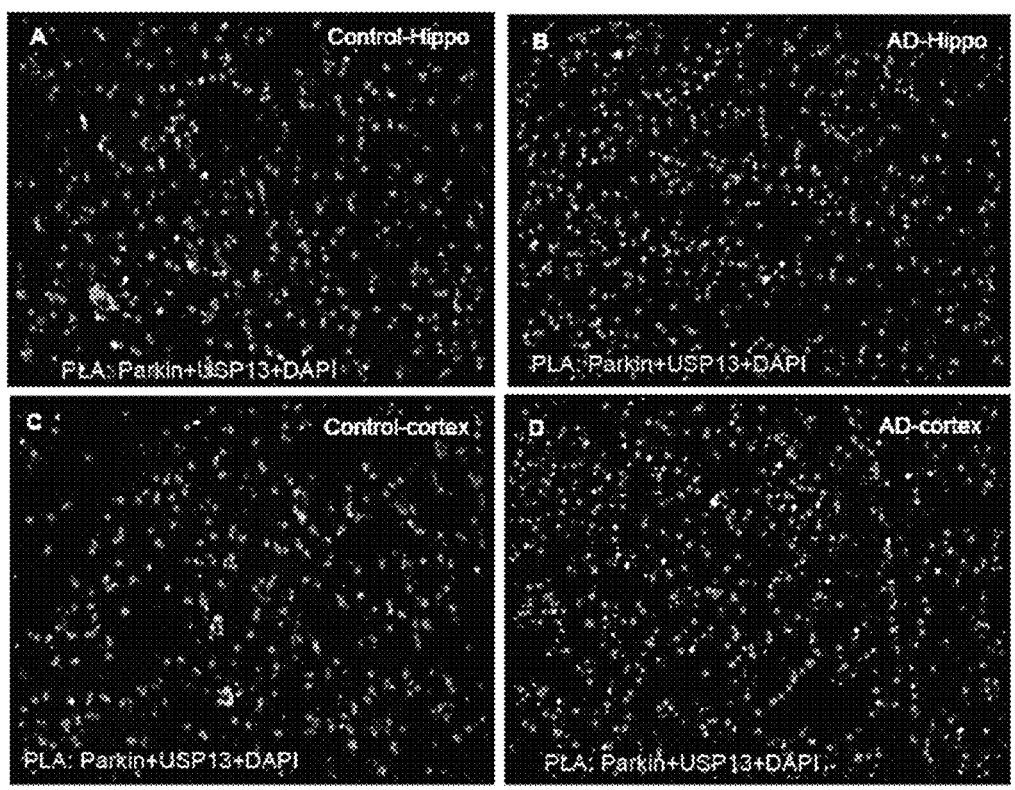
FIG. 4 shows photomicrographs of control (FIGS. 4A, 4C) and post-mortem human AD (FIGS. 4B, 4D) brains, showing that parkin interaction with deubiquitinase (USP-13) is increased in AD. A Proximity Ligation Assay (PLA) in situ on 30 mm thick human brain sections shows parkin and ubiquitin specific peptidase 10 (USP13). The interaction between parkin and ubiquitin specific peptidase 10 (USP13) is increased in hippocampus (FIGS. 4A, 4C) and cortex (FIGS. 4C and 4D) with AD. The increase in USP13 level is paralleled by increased interaction with parkin, indicative of parkin deubiquitination and inactivity, which leads to accumulation and decreased solubility in the human brain.
Figure 5:
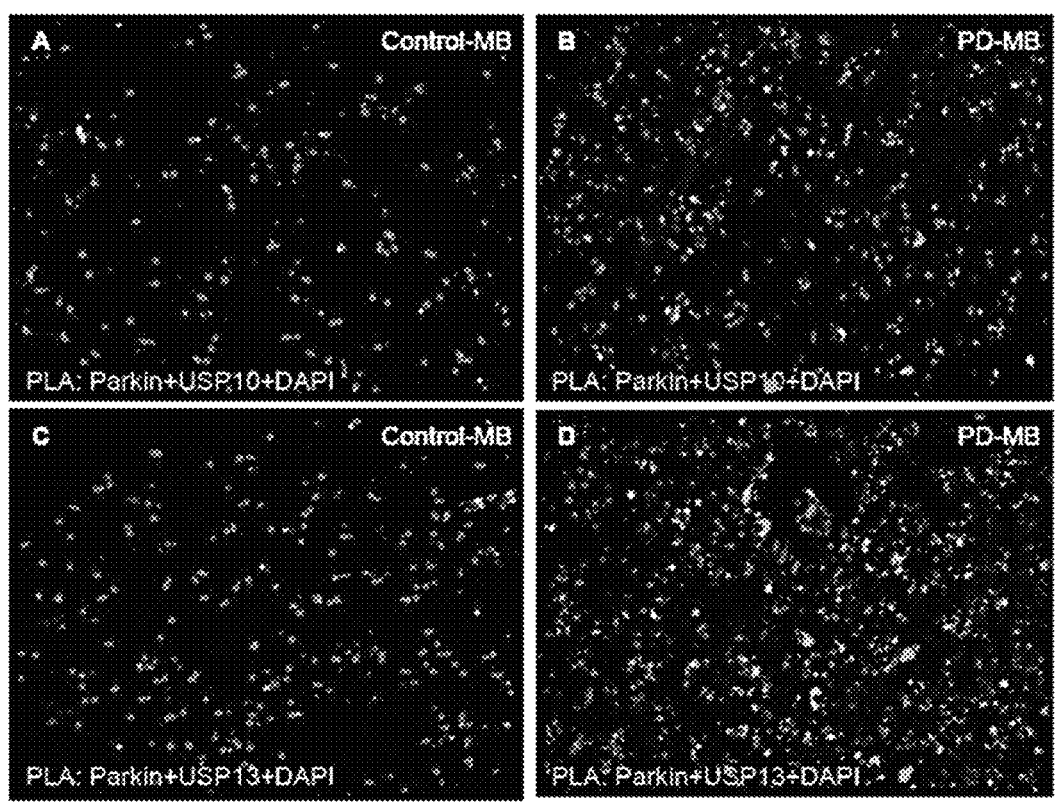
FIG. 5 shows photomicrographs of control (FIGS. 5A, 5C) and post-mortem human PD (FIGS. 5B, 5D) brains showing that parkin interaction with deubiquitinase (USP-10/13) is increased in post-mortem human PD brains. A Proximity Ligation Assay (PLA) in situ on 30 mm thick human brain sections shows parkin and ubiquitin specific peptidase 10/13 (USP10/13). Parkin and ubiquitin specific peptidase 10 (USP10) interaction is increased in human PD midbrain (FIG. 5B) as compared to control (FIG. 5A); and parkin and ubiquitin specific peptidase 13 (USP13) interaction is increased in human PD midbrain (FIG. 5D) as compared to control (FIG. 5C). The increase in USP10/13 level is paralleled by increased interaction with parkin, indicative of parkin de-ubiquitination and inactivity, which leads to accumulation and decreased solubility in the human brain.
Figure 6:
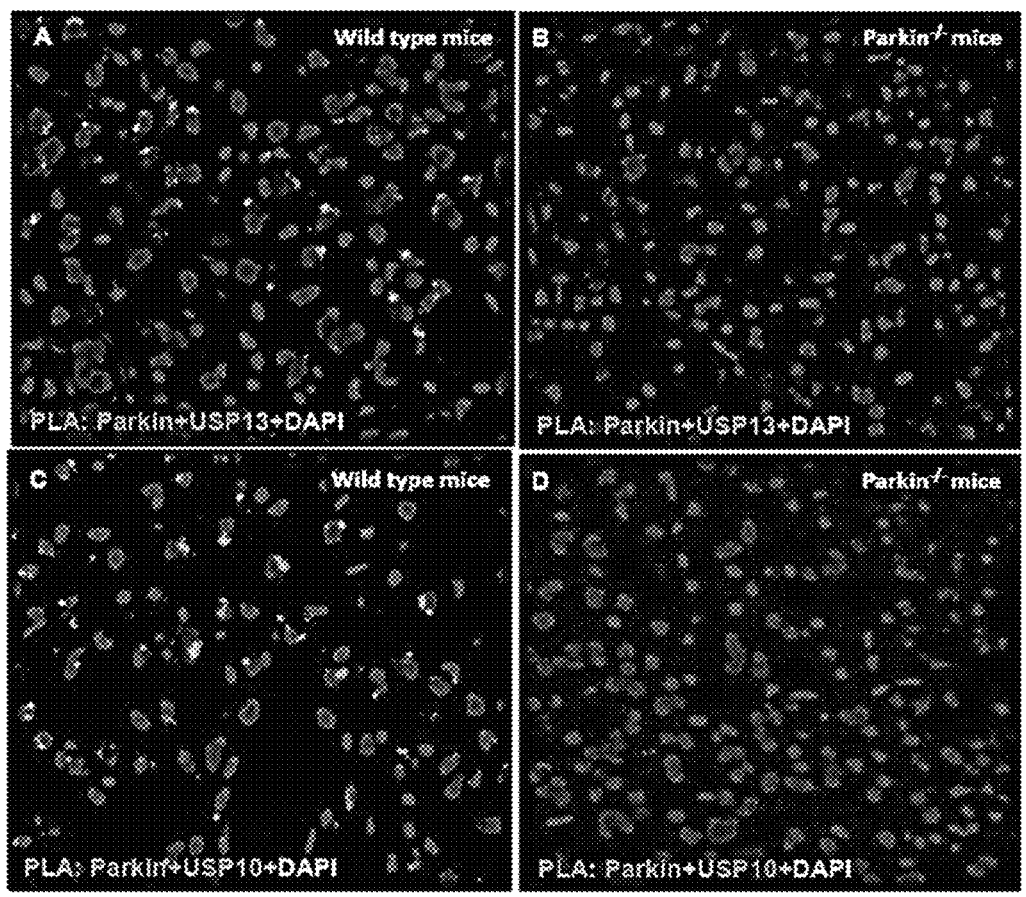
FIG. 6 shows photomicrographs of wild type mouse brain (FIGS. 6A, 6C) and parkin −/− mouse brain (FIGS. 6B, 6D), showing that parkin interacts with deubiquitinating enzymes in wild type but not parkin −/− mice. A Proximity Ligation Assay (PLA) in situ on 20 mm thick brain sections shows parkin and ubiquitin specific peptidase 13 (USP13) interaction in C57BL/6 mice (FIG. 6A) but not parkin−/− mice (FIG. 6B). PLA in situ on 20 mm thick brain sections shows parkin and ubiquitin specific peptidase 10 (USP10) interaction in C57BL/6 (FIG. 6C) mice but not parkin−/− mice (FIG. 6D). These data indicate that parkin could interact with USP10 and 13 under normal conditions.
Figure 7:
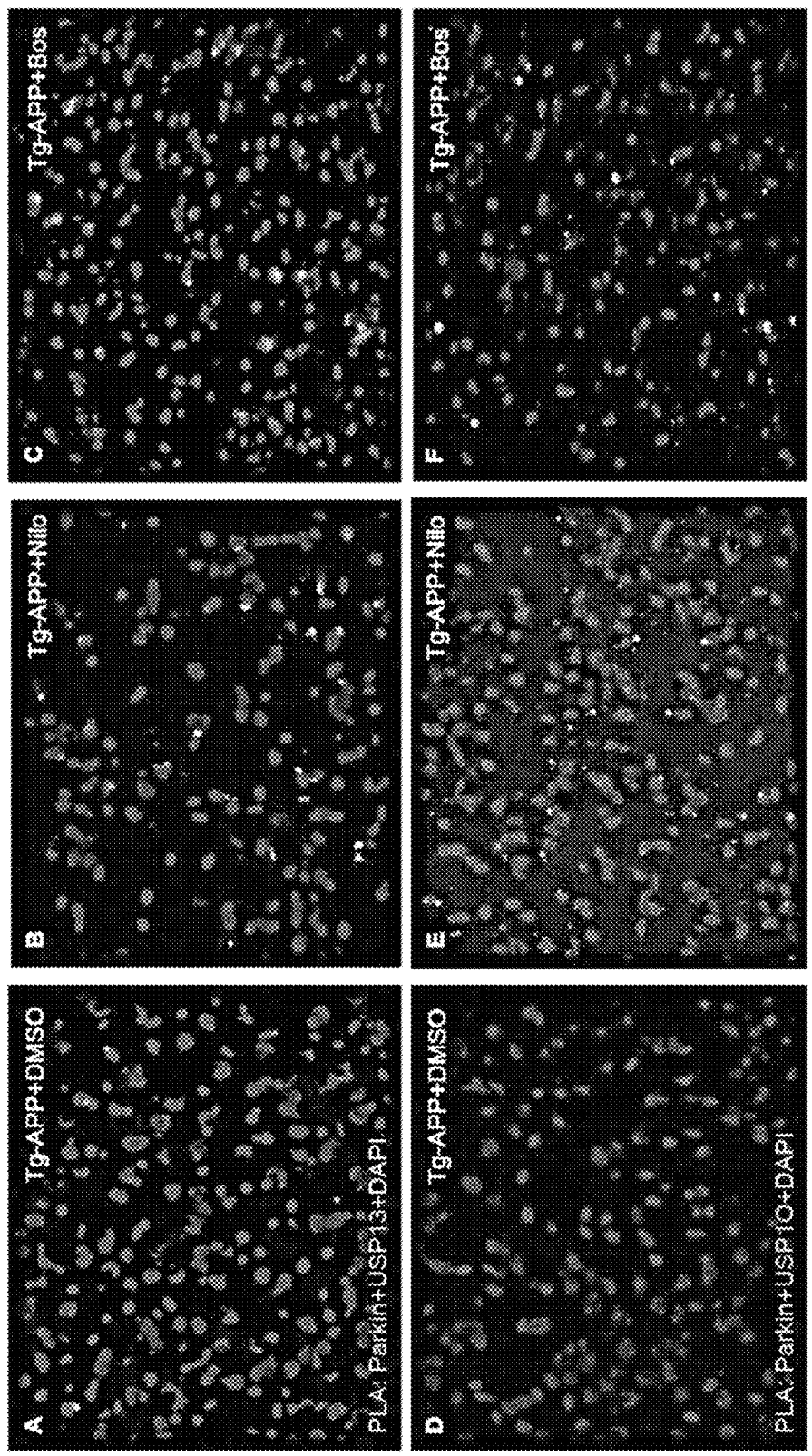
FIG. 7 shows photomicrographs of brain sections from Tg-APP mice, indicating that parkin interaction with deubiquitinating enzymes (DUBs) is decreased in Tg-APP mice and tyrosine kinase inhibition increases parkin-DUBs interaction. A Proximity Ligation Assay (PLA) in situ on 20 mm thick brain sections shows parkin and ubiquitin specific peptidase 13 (USP13) in Tg-APP mice treated with DMSO (FIG. 7A), 10 mg/kg Nilotinib (FIG. 7B), and 5 mg/kg Bosutinib (FIG.

Using proximity ligation assay (PLA), which allows direct observation of individual endogenous protein complexes in situ, it was found that parkin interacts with at least two ubiquitin specific proteases (USP)-13 and 10 (FIGS. 3-5), which are deubiquitination enzymes involved in detaching ubiquitin from parkin, leading to decreased activity or lack of proteasomal degradation. The levels of USP-13 and USP-10 are increased in post-mortem AD and PD brains compared to age-matched controls (FIG. 2). In parallel with the alteration in deubiquitinase levels, parkin soubility is decreased and interaction with beclin-1 is greatly reduced (FIG. 9). Functional parkin-beclin-1 interaction is also lost in Tg-APP and A53T mice (FIGS. 7 and 8). Further, parkin interacts with deubiquitinating enzymes in wild type but not parkin −/− mice (FIG. 6).

FIG. 10 is a schematic diagram showing that amyloid accumulation leads to autophagic induction and sequestration in phagophores. In transgenic or amyloid expressing animals parkin interaction with beclin-1 is reduced, leading to decreased maturation of phagophore into autophagosomes and autophagic defects. Kinase inhibition activates parkin and increases its interaction with beclin-1, resulting in maturation of phagophores into phagosomes and clearance. Also, in human AD and PD brains, parkin-beclin-1 interaction is reduced, indicating that USPs inactivate parkin and prevent functional interaction with beclin-1 to execute autophagic clearance of misfolded amyloid proteins.

Thus, increased levels of USP-13 and 10 in neurodegeneration reduces parkin function and prevents its recycling via proteasomal degradation, leading to decreased solubility and accumulation in disease Inhibition of USP-13 and/or USP-10 and perhaps other deubiquitination enzymes (DUBs) in neurodenegerative diseases, myodegenerative diseases, prion disease and cancer leads to increased parkin activity as a therapeutic strategy.

Also provided herein are the results of experiments showing that treatment with Nilotinib or Bosutinib enhances autophagic clearance (FIGS. 11-25).

Example II

To determine if USP13 deubiquitinates parkin and decreases its stability and E3 ubiquitin ligase activity, several studies were performed.

Parkin levels, solubility and ubiquitination were examined via Western blot (WB), ELISA, Proximity Ligation Assay (PLA) and immunoprecipitation. To evaluate USP13 effects on endogenous parkin in A53T, parkin solubility was determined via fractionation of soluble (supernatant) and insoluble (pellet re-suspended in 4M urea) parkin. Quantitative ELISA (My BioSource, San Diego, Calif. (MBS723678)) and WB was performed with anti-parkin antibodies. To determine whether parkin level correlates with its enzymatic activity, parkin (1:100) was immunoprecipitated with anti-parkin antibody (PRK8) from mouse brain lysates and its E3 ubiquitin ligase activity (with E2:UbcH7) was measured using the E3LITE customizable ubiquitin ligase kit (LifeSensors, Malvern, Pa. (Cat #UC101)).

Immunohistochemistry of Brain Sections

Animals were deeply anesthetized with a mixture of Xylazine and Ketamine (1:8), washed with 1× saline for 1 min and then perfused with 4% paraformaldehyde (PFA) for 15-20 min. Brains were quickly dissected out and immediately stored in 4% PFA for 24 h at 4° C., and then transferred to 30% sucrose at 4° C. for 48 h. Tissues were cut using a cryostat at 4° C. into 20 μm thick sections and stored at −20° C.

Subcellular Fractionation for Isolation of Autophagic Compartments

Animal brains (0.5 grams) were homogenized at low speed (Cole-Palmer, Vernon Hills, Ill. (LabGen 7 Series Homogenizer, 115 Vac)) in 1×STEN buffer and centrifuged at 1,000 g for 10 minutes to isolate the supernatant from the pellet. The pellet was resuspended in 1×STEN buffer and centrifuged once to increase the recovery of lysosomes. The pooled supernatant was centrifuged at 100,000 rpm for 1 hour at 4° C. to extract the pellet containing autophagic vacuoles (AVs) and lysosomes. The pellet was resuspended in 10 ml (0.33 g/ml) 50% Metrizamide and 10 ml deionized water in cellulose nitrate tubes. A discontinuous Metrizamide gradient was constructed in layers from bottom to top as follows: 6 ml of pellet suspension, 10 ml of 26%; 5 ml of 24%; 5 ml of 20%; and 5 ml of 10% Metrizamide. After centrifugation at 10,000 rpm for 1 hour at 4° C., the fraction floating on the 10% layer (Lysosome) and the fractions banding at the 24%/20% (AV 20) and the 20%/10% (AV10) Metrizamide interphases were collected by syringe and examined.

Proximity Ligation Assay

Primary 1:100 mouse anti-parkin and rabbit 1:100 anti-ubiquitin antibodies were applied to 20 μm thick sections of mouse brain overnight at 4° C. A Duolink® In Situ Red Starter Kit (Sigma Aldrich, St. Louis, Mo. (Cat #92101-KI01)) containing species-specific secondary antibodies or PLA probes, each with a unique short DNA strand attached to it (Axxora, LLC, Farmingdale, N.Y.) was used as described in the manufacturer's protocol. When the PLA probes are in close proximity, the DNA strands interact through subsequent addition of two other circle-forming DNA oligonucleotides. After joining of the two added oligonucleotides by enzymatic ligation, they are amplified via rolling circle amplification using a polymerase to highlight the interaction. Fluorescence in each single-molecule amplification product is easily visible as a distinct bright spot when viewed with a fluorescence microscope.

USP 13 and Parkin

Ubiquitination involves the attachment of a 76-amino acid ubiquitin moiety to a protein via an isopeptide linkage that is formed between the C-terminal glycine of ubiquitin and the ϵ-amino acid side chain of a Lys residue within the target protein. Conjugation of ubiquitin to a protein is a multistep process requiring three different enzymes, including the E1 ubiquitin-activating and E2 conjugating enzymes and interaction with the E3 ubiquitin ligase. Parkin is an E3 RING ubiquitin ligase, which provides a scaffold through which the E3 interacts with the E2-ubiquitin to facilitate the transfer of ubiquitin from the E2 onto the substrate protein.

Human M17 neuroblastoma cells, which express parkin mRNA but quickly degrade the protein, were transfected with lentiviral plasmids containing LacZ, parkin and USP13 cDNAs (3 μg) in 12 well dishes for 48 hr. Western blot (WB) analysis of soluble (STEN) extracts showed that USP13 expression was significantly (84%) increased relative to actin in transfected cells (FIGS. 26A&B, $1^{st}$ blot, p<0.05) but the level of USP10 was unaffected (FIG. 26A, $2^{nd}$ blot) compared to LacZ transfected cells. The expression level of parkin was undetected in LacZ transfected cells (FIG. 26A, $3^{rd}$ blot), but co-expression of parkin and USP13 resulted in a significant increase of soluble parkin relative to actin (210%) compared to parkin transfected cells (FIGS. 26A and D), suggesting that USP13 increases parkin level (N=7, P<0.05). USP13 could alter parkin levels via de-ubiquitination and decreased protein solubility, therefore the insoluble fraction was extracted from the pellets in 4M urea. Co-expression of parkin and USP13 also led to a significant increase (160%) in insoluble parkin relative to actin (FIGS. 26C and D) compared to cells transfected with parkin alone (N=7, p<0.05). To determine whether USP13 can deubiquitinate parkin, rat B35 neuroblastoma cells were transfected with lentiviral wild type or the non-catalytic mutant T240R parkin with and without USP13. This cell line was used instead of the human M17 cells in order to immunoprecipitate parkin without overexpression or proteasomal inhibition. Parkin immunoprecipitation and Western blot with anti-ubiquitin antibodies showed decreased ubiquitinated parkin level when parkin was co-expressed with USP13 (FIG. 26E, $1^{st}$ blot) compared to parkin expression alone or the input (N=7). However, the level of ubiquitinated proteins when mutant T240R parkin was expressed was unaltered in the presence or absence of USP13 compared to wild type parkin (FIG. 26E), showing that wild type but not mutant T240R parkin can be deubiquitinated by USP13.

To verify that USP13 is a parkin deubiquitinase, parkin and USP13 were separately immunoprecipitated from transfected cells and incubated with recombinant E1, E2 and ATP using a Customizable Ubiquitin Ligase E3LITE Kit (Life Sensors, UC#101), which measures the mechanisms of E1-E2-E3 activity. Parkin and USP13 were added to UbcH7 as an E2 that provides maximum activity with parkin E3 ligase in the presence of E1 and recombinant ubiquitin, including WT containing all seven possible surface Lys or no Lys mutant (K0, negative control). The mix was added to an ELISA microplate that captures polyubiquitin chains formed in the E3-dependent reaction. Poly-ubiquitin chains were used as positive controls (FIG. 26F). No parkin activity was detected with K0 ubiquitin, but parkin was ubiquitinated using WT ubiquitin suggesting parkin activity. However, USP13 significantly decreased (36%) parkin ubiquitination (FIG. 26F, p<0.05, N=7), showing decreased parkin activity in the presence of USP13.

To further determine whether USP13 targets parkin, M17 cells were transfected with 3 μg lentiviral plasmids containing parkin, USP13 or different shRNA USP13 clones (FIG. 27A) for 48 hr. The expression level of the shRNAs was determined by routine stereology of the GFP and VS-tagged lentivirus to ensure equal expression of lentiviral plasmids. USP13 gene expression level is verified by PCR. Co-expression of USP13 and parkin led to an increase (134%) in parkin level compared to parkin alone (FIG. 27A, $1^{st}$ blot, N=4), but shRNA expression reduced USP13 and parkin levels relative to actin (FIG. 27A). E08 shRNA (5' TATTCGTTGCTCGTAGTGC 3'(SEQ ID NO: 5)) did not produce any significant effects on USP13 (FIG. 27A, $1^{st}$ blot) or USP10 ($2^{nd}$ blot) or parkin ($3^{rd}$ blot), but 4 other shRNAs including, E07 (5' TTTCCAGTGAAGTACACAG 3' (SEQ ID NO: 1)); F04 (5'AACTTAGTCATCTGTGTGT 3' (SEQ ID NO: 2)); F03 (5' TTTCTCGCAGGTCGCATCT 3' (SEQ ID NO: 3)) and F02 (5' TCTTGTAGACCCTGTCGCC 3' (SEQ ID NO: 4)) significantly reduced USP13 (60-70%), without any effects on USP10, but also significantly reduced (55-70%) parkin levels relative to actin compared to USP13 (FIG. 3A, p<0.05, N=4). These data show that USP13 overexpression increases parkin levels, while USP13 blockage with shRNA decreases parkin, perhaps due to increased protein degradation. To ascertain that manipulation of USP13 expression affects protein clearance, the activity of the 20S proteasome activity was measured using chymotrypsin-like assays. Proteasome activity was inhibited after 2 hr treatment with 20 μM proteasome inhibitor MG132 compared to control (LacZ) or parkin alone (FIG. 27B, N=4). Co-expression of USP13 with parkin significantly reduced proteasome activity (34%) compared to parkin (N=4, p<0.05) and MG132 further inhibited the proteasome. However, blocking USP13 with shRNA (F03) significantly increased proteasome activity compared to control (14%) and both F03 and F02 completely reversed the effects of USP13 overexpression on proteasome activity, while MG132 blocked these effects. Taken together, these data show that USP13 expression can deubiquitinate parkin, leading to decreased protein solubility and accumulation, whereas blocking USP13 expression reduces parkin level via decreased deubiquitination and enhanced proteasomal clearance.

Human M17 cells were transfected with USP13 cDNAs and shRNAs in the presence of Tau and ELISA was performed showing the level of hyperphosphorylated Tau at Ser 396 in the presence of parkin (FIG. 28A) the presence and B) absence of parkin. These data show that USP13 deletion can increase parkin-mediated Tau clearance.

Human M17 cells were transfected with USP13 cDNAs and shRNAs in the presence of αβ42. ELISA was performed showing the level of αβ42 and hyperphosphorylated Tau at Ser 396 in the presence of parkin (FIGS. 29A and B) and in the absence of parkin (FIGS. 29C and D). These data show that USP13 deletion can increase parkin-mediated amyloid clearance.

In summary, ubiquitinated parkin is activated in response to amyloid (alpha-Synuclein, beta-amyloid, Tau and TDP-43) accumulation, leading to facilitation of clearance. An increase in USP13 leads to parkin deubiquitination and decreased activity, resulting in misfolded protein accumulation in neurodegenerative diseases (FIG. 30A). It is likely that ubiquitination activates parkin, which is then recycled through the proteasome to prevent its accumulation (FIG. 30B). Activated parkin facilitates autophagic clearance. The studies provided herein show that an increase in USP13 leads to parkin deubiquitination and decreased proteasomal recognition, leading to its instability/insolubility and accumulation. This results in subsequent autophagic failure and death of neurons. Therefore, inhibitors of USP13 are useful for the treatment of diseases such as neurodegenerative diseases, a myodegenerative diseases, prion diseases or cancer.

What is claimed is:

1. A method of promoting parkin activity in a subject that has a neurodegenerative disease of the central nervous system, a myodegenerative disease or a prion disease, comprising:
   a) selecting a subject with a disorder associated with decreased parkin activity, wherein the disorder is a neurodegenerative disease of the central nervous system, a myodegenerative disease or a prion disease, wherein the neurodegenerative disease is selected from the group consisting of Amyotrophic Lateral Sclerosis, Alzheimer's Disease, Parkinson's Disease, Huntington's Disease, and Mild Cognitive Impairment, an α-Synucleinopathy and a Tauopathy; and
   b) administering to the subject an effective amount of a composition that increases parkin activity, wherein the composition is an inhibitor of a deubiquitinating enzyme.

2. The method of claim 1, wherein the deubiquitinating enzyme is USP-10 or USP-13.

3. The method of claim 1, wherein the composition increases parkin activity by promoting the interaction between parkin and beclin-1.

4. The method of claim 1, wherein the composition inhibits deubiquitination of parkin.

5. A method of treating a neurodegenerative disease, a myodegenerative disease or prion disease in a subject, comprising:
   a) selecting a subject with a neurodegenerative disease of the central nervous system, a myodegenerative disease, or a prion disease, wherein the neurodegenerative disease is selected from the group consisting of Amyotrophic Lateral Sclerosis, Alzheimer's Disease, Parkinson's Disease, Huntington's Disease, and Mild Cognitive Impairment, an α-Synucleinopathy and a Tauopathy; and
   b) administering to the subject an effective amount of a composition that increases parkin activity, wherein the composition is an inhibitor of a deubiquitinating enzyme.

6. The method of claim 5, wherein the deubiquitinating enzyme is USP-10 or USP-13.

7. The method of claim 5, wherein the composition promotes the interaction between parkin and beclin-1.

8. The method of claim 5, wherein the composition inhibits deubiquitination of parkin.

* * * * *

SEQUENCE LISTING

```
<160> NUMBER OF SEQ ID NOS: 14

<210> SEQ ID NO 1
<211> LENGTH: 19
<212> TYPE: DNA
<213> ORGANISM: Artificial sequence
<220> FEATURE:
<223> OTHER INFORMATION: Synthetic construct

<400> SEQUENCE: 1
tttccagtga agtacacag                                                  19

<210> SEQ ID NO 2
<211> LENGTH: 19
<212> TYPE: DNA
<213> ORGANISM: Artificial sequence
<220> FEATURE:
<223> OTHER INFORMATION: Synthetic construct

<400> SEQUENCE: 2
aacttagtca tctgtgtgt                                                  19

<210> SEQ ID NO 3
<211> LENGTH: 19
<212> TYPE: DNA
<213> ORGANISM: Artificial sequence
<220> FEATURE:
<223> OTHER INFORMATION: Synthetic construct

<400> SEQUENCE: 3
tttctcgcag gtcgcatct                                                  19

<210> SEQ ID NO 4
<211> LENGTH: 19
<212> TYPE: DNA
<213> ORGANISM: Artificial sequence
<220> FEATURE:
<223> OTHER INFORMATION: Synthetic construct

<400> SEQUENCE: 4
```
tcttgtagac cctgtcgcc 19

<210> SEQ ID NO 5
<211> LENGTH: 19
<212> TYPE: DNA
<213> ORGANISM: Artificial sequence
<220> FEATURE:
<223> OTHER INFORMATION: Synthetic construct

<400> SEQUENCE: 5
tattcgttgc tcgtagtgc 19

<210> SEQ ID NO 6
<211> LENGTH: 802
<212> TYPE: PRT
<213> ORGANISM: Homo sapiens

<400> SEQUENCE: 6

```
Met Pro Trp Leu Pro Ser Pro Gly Ile Gly Gln Tyr Ile Phe Gly Asp
1               5                   10                  15

Phe Ser Pro Asp Glu Phe Asn Gln Phe Phe Val Thr Pro Arg Ser Ser
                20                  25                  30

Val Glu Leu Pro Pro Tyr Ser Gly Thr Val Leu Cys Gly Thr Gln Ala
            35                  40                  45

Val Asp Lys Leu Pro Asp Gly Gln Glu Tyr Gln Arg Ile Glu Phe Gly
50                  55                  60

Val Asp Glu Val Ile Glu Pro Ser Asp Thr Leu Pro Arg Thr Pro Ser
65                  70                  75                  80

Tyr Ser Ile Ser Ser Thr Leu Asn Pro Gln Ala Pro Glu Phe Ile Leu
                85                  90                  95

Gly Cys Thr Ala Ser Lys Ile Thr Pro Asp Gly Ile Thr Lys Glu Ala
            100                 105                 110

Ser Tyr Gly Ser Ile Asp Cys Gln Tyr Pro Gly Ser Ala Leu Ala Leu
        115                 120                 125

Asp Gly Ser Ser Asn Val Glu Ala Glu Val Leu Glu Asn Asp Gly Val
    130                 135                 140

Ser Gly Gly Leu Gly Gln Arg Glu Arg Lys Lys Lys Lys Arg Pro
145                 150                 155                 160

Pro Gly Tyr Tyr Ser Tyr Leu Lys Asp Gly Gly Asp Ser Ile Ser
                165                 170                 175

Thr Glu Ala Leu Val Asn Gly His Ala Asn Ser Ala Val Pro Asn Ser
            180                 185                 190

Val Ser Ala Glu Asp Ala Glu Phe Met Gly Asp Met Pro Pro Ser Val
        195                 200                 205

Thr Pro Arg Thr Cys Asn Ser Pro Gln Asn Ser Thr Asp Ser Val Ser
    210                 215                 220

Asp Ile Val Pro Asp Ser Pro Phe Pro Gly Ala Leu Gly Ser Asp Thr
225                 230                 235                 240

Arg Thr Ala Gly Gln Pro Glu Gly Gly Pro Gly Ala Asp Phe Gly Gln
                245                 250                 255

Ser Cys Phe Pro Ala Glu Ala Gly Arg Asp Thr Leu Ser Arg Thr Ala
            260                 265                 270

Gly Ala Gln Pro Cys Val Gly Thr Asp Thr Thr Glu Asn Leu Gly Val
        275                 280                 285

Ala Asn Gly Gln Ile Leu Glu Ser Ser Gly Glu Gly Thr Ala Thr Asn
    290                 295                 300
```

-continued

Gly Val Glu Leu His Thr Thr Glu Ser Ile Asp Leu Asp Pro Thr Lys
305                 310                 315                 320

Pro Glu Ser Ala Ser Pro Ala Asp Gly Thr Gly Ser Ala Ser Gly
            325                 330                 335

Thr Leu Pro Val Ser Gln Pro Lys Ser Trp Ala Ser Leu Phe His Asp
            340                 345                 350

Ser Lys Pro Ser Ser Ser Pro Val Ala Tyr Val Glu Thr Lys Tyr
            355                 360                 365

Ser Pro Pro Ala Ile Ser Pro Leu Val Ser Glu Lys Gln Val Glu Val
    370                 375                 380

Lys Glu Gly Leu Val Pro Val Ser Glu Asp Pro Val Ala Ile Lys Ile
385                 390                 395                 400

Ala Glu Leu Leu Glu Asn Val Thr Leu Ile His Lys Pro Val Ser Leu
                405                 410                 415

Gln Pro Arg Gly Leu Ile Asn Lys Gly Asn Trp Cys Tyr Ile Asn Ala
            420                 425                 430

Thr Leu Gln Ala Leu Val Ala Cys Pro Pro Met Tyr His Leu Met Lys
            435                 440                 445

Phe Ile Pro Leu Tyr Ser Lys Val Gln Arg Pro Cys Thr Ser Thr Pro
450                 455                 460

Met Ile Asp Ser Phe Val Arg Leu Met Asn Glu Phe Thr Asn Met Pro
465                 470                 475                 480

Val Pro Pro Lys Pro Arg Gln Ala Leu Gly Asp Lys Ile Val Arg Asp
            485                 490                 495

Ile Arg Pro Gly Ala Ala Phe Glu Pro Thr Tyr Ile Tyr Arg Leu Leu
            500                 505                 510

Thr Val Asn Lys Ser Ser Leu Ser Glu Lys Gly Arg Gln Glu Asp Ala
            515                 520                 525

Glu Glu Tyr Leu Gly Phe Ile Leu Asn Gly Leu His Glu Glu Met Leu
530                 535                 540

Asn Leu Lys Lys Leu Leu Ser Pro Ser Asn Glu Lys Leu Thr Ile Ser
545                 550                 555                 560

Asn Gly Pro Lys Asn His Ser Val Asn Glu Glu Glu Gln Glu Gln
            565                 570                 575

Gly Glu Gly Ser Glu Asp Glu Trp Glu Gln Val Gly Pro Arg Asn Lys
            580                 585                 590

Thr Ser Val Thr Arg Gln Ala Asp Phe Val Gln Thr Pro Ile Thr Gly
            595                 600                 605

Ile Phe Gly Gly His Ile Arg Ser Val Val Tyr Gln Gln Ser Ser Lys
    610                 615                 620

Glu Ser Ala Thr Leu Gln Pro Phe Phe Thr Leu Gln Leu Asp Ile Gln
625                 630                 635                 640

Ser Asp Lys Ile Arg Thr Val Gln Asp Ala Leu Glu Ser Leu Val Ala
            645                 650                 655

Arg Glu Ser Val Gln Gly Tyr Thr Thr Lys Thr Lys Gln Glu Val Glu
            660                 665                 670

Ile Ser Arg Arg Val Thr Leu Glu Lys Leu Pro Pro Val Leu Val Leu
            675                 680                 685

His Leu Lys Arg Phe Val Tyr Glu Lys Thr Gly Gly Cys Gln Lys Leu
            690                 695                 700

Ile Lys Asn Ile Glu Tyr Pro Val Asp Leu Glu Ile Ser Lys Glu Leu
705                 710                 715                 720

Leu Ser Pro Gly Val Lys Asn Lys Asn Phe Lys Cys His Arg Thr Tyr

```
                        725                 730                 735
Arg Leu Phe Ala Val Val Tyr His His Gly Asn Ser Ala Thr Gly Gly
                740                 745                 750

His Tyr Thr Thr Asp Val Phe Gln Ile Gly Leu Asn Gly Trp Leu Arg
                755                 760                 765

Ile Asp Asp Gln Thr Val Lys Val Ile Asn Gln Tyr Gln Val Val Lys
                770                 775                 780

Pro Thr Ala Glu Arg Thr Ala Tyr Leu Leu Tyr Tyr Arg Arg Val Asp
785                 790                 795                 800

Leu Leu

<210> SEQ ID NO 7
<211> LENGTH: 798
<212> TYPE: PRT
<213> ORGANISM: Homo sapiens

<400> SEQUENCE: 7

Met Ala Leu His Ser Pro Gln Tyr Ile Phe Gly Asp Phe Ser Pro Asp
1               5                   10                  15

Glu Phe Asn Gln Phe Phe Val Thr Pro Arg Ser Ser Val Glu Leu Pro
                20                  25                  30

Pro Tyr Ser Gly Thr Val Leu Cys Gly Thr Gln Ala Val Asp Lys Leu
            35                  40                  45

Pro Asp Gly Gln Glu Tyr Gln Arg Ile Glu Phe Gly Val Asp Glu Val
        50                  55                  60

Ile Glu Pro Ser Asp Thr Leu Pro Arg Thr Pro Ser Tyr Ser Ile Ser
65                  70                  75                  80

Ser Thr Leu Asn Pro Gln Ala Pro Glu Phe Ile Leu Gly Cys Thr Ala
                85                  90                  95

Ser Lys Ile Thr Pro Asp Gly Ile Thr Lys Glu Ala Ser Tyr Gly Ser
                100                 105                 110

Ile Asp Cys Gln Tyr Pro Gly Ser Ala Leu Ala Leu Asp Gly Ser Ser
            115                 120                 125

Asn Val Glu Ala Glu Val Leu Glu Asn Asp Gly Val Ser Gly Gly Leu
        130                 135                 140

Gly Gln Arg Glu Arg Lys Lys Lys Lys Arg Pro Pro Gly Tyr Tyr
145                 150                 155                 160

Ser Tyr Leu Lys Asp Gly Gly Asp Asp Ser Ile Ser Thr Glu Ala Leu
                165                 170                 175

Val Asn Gly His Ala Asn Ser Ala Val Pro Asn Ser Val Ser Ala Glu
                180                 185                 190

Asp Ala Glu Phe Met Gly Asp Met Pro Pro Ser Val Thr Pro Arg Thr
            195                 200                 205

Cys Asn Ser Pro Gln Asn Ser Thr Asp Ser Val Ser Asp Ile Val Pro
        210                 215                 220

Asp Ser Pro Phe Pro Gly Ala Leu Gly Ser Asp Thr Arg Thr Ala Gly
225                 230                 235                 240

Gln Pro Glu Gly Gly Pro Gly Ala Asp Phe Gly Gln Ser Cys Phe Pro
                245                 250                 255

Ala Glu Ala Gly Arg Asp Thr Leu Ser Arg Thr Ala Gly Ala Gln Pro
                260                 265                 270

Cys Val Gly Thr Asp Thr Thr Glu Asn Leu Gly Val Ala Asn Gly Gln
            275                 280                 285

Ile Leu Glu Ser Ser Gly Glu Gly Thr Ala Thr Asn Gly Val Glu Leu
```

```
                290                 295                 300
His Thr Thr Glu Ser Ile Asp Leu Asp Pro Thr Lys Pro Glu Ser Ala
305                 310                 315                 320

Ser Pro Pro Ala Asp Gly Thr Gly Ser Ala Ser Gly Thr Leu Pro Val
                325                 330                 335

Ser Gln Pro Lys Ser Trp Ala Ser Leu Phe His Asp Ser Lys Pro Ser
                340                 345                 350

Ser Ser Ser Pro Val Ala Tyr Val Glu Thr Lys Tyr Ser Pro Pro Ala
            355                 360                 365

Ile Ser Pro Leu Val Ser Glu Lys Gln Val Glu Val Lys Glu Gly Leu
        370                 375                 380

Val Pro Val Ser Glu Asp Pro Val Ala Ile Lys Ile Ala Glu Leu Leu
385                 390                 395                 400

Glu Asn Val Thr Leu Ile His Lys Pro Val Ser Leu Gln Pro Arg Gly
                405                 410                 415

Leu Ile Asn Lys Gly Asn Trp Cys Tyr Ile Asn Ala Thr Leu Gln Ala
                420                 425                 430

Leu Val Ala Cys Pro Pro Met Tyr His Leu Met Lys Phe Ile Pro Leu
            435                 440                 445

Tyr Ser Lys Val Gln Arg Pro Cys Thr Ser Thr Pro Met Ile Asp Ser
        450                 455                 460

Phe Val Arg Leu Met Asn Glu Phe Thr Asn Met Pro Val Pro Pro Lys
465                 470                 475                 480

Pro Arg Gln Ala Leu Gly Asp Lys Ile Val Arg Asp Ile Arg Pro Gly
                485                 490                 495

Ala Ala Phe Glu Pro Thr Tyr Ile Tyr Arg Leu Leu Thr Val Asn Lys
            500                 505                 510

Ser Ser Leu Ser Glu Lys Gly Arg Gln Glu Asp Ala Glu Glu Tyr Leu
        515                 520                 525

Gly Phe Ile Leu Asn Gly Leu His Glu Glu Met Leu Asn Leu Lys Lys
        530                 535                 540

Leu Leu Ser Pro Ser Asn Glu Lys Leu Thr Ile Ser Asn Gly Pro Lys
545                 550                 555                 560

Asn His Ser Val Asn Glu Glu Gln Glu Gln Gly Glu Gly Ser
                565                 570                 575

Glu Asp Glu Trp Glu Gln Val Gly Pro Arg Asn Lys Thr Ser Val Thr
            580                 585                 590

Arg Gln Ala Asp Phe Val Gln Thr Pro Ile Thr Gly Ile Phe Gly Gly
        595                 600                 605

His Ile Arg Ser Val Val Tyr Gln Gln Ser Ser Lys Glu Ser Ala Thr
        610                 615                 620

Leu Gln Pro Phe Phe Thr Leu Gln Leu Asp Ile Gln Ser Asp Lys Ile
625                 630                 635                 640

Arg Thr Val Gln Asp Ala Leu Glu Ser Leu Val Ala Arg Glu Ser Val
                645                 650                 655

Gln Gly Tyr Thr Thr Lys Thr Lys Gln Glu Val Glu Ile Ser Arg Arg
            660                 665                 670

Val Thr Leu Glu Lys Leu Pro Pro Val Leu Val Leu His Leu Lys Arg
        675                 680                 685

Phe Val Tyr Glu Lys Thr Gly Gly Cys Gln Lys Leu Ile Lys Asn Ile
        690                 695                 700

Glu Tyr Pro Val Asp Leu Glu Ile Ser Lys Glu Leu Leu Ser Pro Gly
705                 710                 715                 720
```

```
Val Lys Asn Lys Asn Phe Lys Cys His Arg Thr Tyr Arg Leu Phe Ala
            725                 730                 735

Val Val Tyr His His Gly Asn Ser Ala Thr Gly Gly His Tyr Thr Thr
            740                 745                 750

Asp Val Phe Gln Ile Gly Leu Asn Gly Trp Leu Arg Ile Asp Asp Gln
            755                 760                 765

Thr Val Lys Val Ile Asn Gln Tyr Gln Val Val Lys Pro Thr Ala Glu
            770                 775                 780

Arg Thr Ala Tyr Leu Leu Tyr Tyr Arg Arg Val Asp Leu Leu
785                 790                 795

<210> SEQ ID NO 8
<211> LENGTH: 3520
<212> TYPE: DNA
<213> ORGANISM: Homo sapiens

<400> SEQUENCE: 8
ctccccgcgc ccgcggcgc gcggccagtg cgcaggcgcg gcggccgatg cgagtgtgta      60
tgtgcgggcg agaagatggc ggcggcgggg gaagcagcgt gagcagccgg aggatcgcgg     120
agtcccaatg aaacgggcag ccatggcccct ccacagcccg cagctcctgg ccatgatcc    180 cattttcatc agatgacttg agaacccaga agctctacca gcactgccat tctgtcccgt    240
cttgaaacat catgccctgg ttgccctctc ctggaatagg gcagtatatt tttggagatt    300
ttagccctga tgaattcaat caattctttg tgactcctcg atcttcagtt gagcttcctc    360
catacagtgg aacagttctg tgtggcacac aggctgtgga taaactacct gatggacaag    420
aatatcagag aattgagttt ggtgtcgatg aagtcattga acccagtgac actttgccga    480 gaaccccccag ctacagtatt tcaagcacac tgaaccctca ggcccctgaa tttattctcg    540
gttgtacagc ttccaaaata accctgatg gtatcactaa agaagcaagc tatggctcca    600
tcgactgcca gtacccaggc tctgccctcg ctttggatgg aagttctaat gtggaggcgg    660
aagttttgga aaatgatggt gtctcaggtg gtcttggaca aagggagcgt aaaaagaaga    720
aaaagcggcc acctggatat tacagctatt tgaaagatgg tggcgatgat agtatctcca    780
cagaagccct ggtcaatggc catgccaatt cagcagtccc gaacagtgtc agtgcagagg    840
atgcagaatt tatgggtgac atgccccgt cagttacgcc caggacttgt aacagccccc    900
agaactccac agactctgtc agtgacattg tgcctgacag tcctttcccc ggagcactcg    960
gcagtgacac caggactgca gggcagccag agggggggccc cggggctgat tttggtcagt   1020
cctgcttccc tgcagaggct ggcagagaca ccctgtcaag gacagctggg gctcagccct   1080
gcgttggtac cgatactact gaaaaccttg gagttgctaa tggacaaata cttgaatcct   1140
cgggtgaggg cacagctacc aacggggtgg agttgcacac cacggaaagc atagacttgg   1200
acccaaccaa acccgagagt gcatcacctc ctgctgacgg cacgggctct gcatcaggca   1260
cccttcctgt cagccagccc aagtcctggg ccagcctctt tcatgattct aagccctctt   1320
cctcctcgcc ggtggcctat gtggaaacta gtattccccc tccgccata tctcccctgg   1380 tttctgaaaa gcaggttgaa gtcaaagaag gccttgttcc ggtttcagag atcctgtag    1440 ccataaagat tgcagagttg ctggagaatg taaccctaat ccataaacca gtgtcgttgc    1500
aaccccgtgg gctgatcaat aaagggaact ggtgctacat taatgctaca ctgcaggcat    1560
tggttgcttg cccgccgatg taccacctga tgaagttcat tcctctgtat tccaaagtgc    1620
aaaggccttg tacgtcaaca cccatgatag acagctttgt tcggctaatg aatgagttca    1680
```

| | |
|---|---|
| ctaatatgcc agtacctcca aaaccccgac aagctcttgg agataaaatc gtgagggata | 1740 |
| ttcgccctgg agctgccttt gagcccacat atatttacag actcctgaca gttaacaagt | 1800 |
| caagcctgtc tgaaaagggt cgacaagaag atgctgagga atacttaggc ttcattctaa | 1860 |
| atggacttca tgaggaaatg ttgaacctaa agaagcttct ctcaccaagt aatgaaaaac | 1920 |
| ttacgatttc caacggcccc aaaaaccact cggtcaatga agaagagcag gaagaacaag | 1980 |
| gtgaaggaag cgaggatgaa tgggaacaag tgggcccccg aacaagact tccgtcaccc | 2040 |
| gccaggcgga ttttgttcag actccaatca ccggcatttt tggtggacac atcaggtctg | 2100 |
| tggtttacca gcagagttca aaagaatctg ccactttgca gccattttc acgttgcagt | 2160 |
| tggatatcca gtcagacaag atacgcacag tccaggatgc actggagagc ttggtggcaa | 2220 |
| gagaatctgt ccaaggttat accacaaaaa ccaaacaaga ggttgagata agtcgaagag | 2280 |
| tgactctgga aaaactccct cctgtcctcg tgctgcacct gaaacgattc gtttatgaga | 2340 |
| agactggtgg gtgccagaag cttatcaaaa atattgaata tcctgtggac ttggaaatta | 2400 |
| gtaaagaact gctttctcca ggggttaaaa ataagaattt taaatgccac cgaacctatc | 2460 |
| ggctctttgc agtggtctac catcacggca acagtgcgac gggcggccat tacactacag | 2520 |
| acgtcttcca gatcggtctg aatggctggc tgcgcatcga tgaccagaca gtcaaggtga | 2580 |
| tcaaccagta ccaggtggtg aaaccaactg ctgaacgcac agcctacctc ctgtattacc | 2640 |
| gccgagtgga cctgctgtaa accctgtgtg cgctgtgtgt gcgcccagtg cccgcttcgt | 2700 |
| aggacaccac ctcacactca cttcccgcct ctctttagtg gctctttaga gagaaactct | 2760 |
| ttctcccttt gcaaaaatgg gctagaatga aaggagatg ccttggggtt cgtgcacaac | 2820 |
| acagcttctg ttgactctaa cttccaaatc aaaatcattt ggttgaaaca gactgttgct | 2880 |
| tgattttaga aaatacacaa aaacccatat ttctgaaata atgctgattc ctgagataag | 2940 |
| aaagtggatt tgatccccag tctcattgct tagtagaata atcctgcac cagcaacaac | 3000 |
| acttgtaaat ttgtgaaaat gaattttatc tttccttaaa aagaaattt tttaatccat | 3060 |
| cacactttc ttccctaccc tttagttttt gataaatgat aaaaatgagc cagttatcaa | 3120 |
| agaagaacta gttcttactt caaaagaaaa ataaacataa aaaataagtt gctggttcct | 3180 |
| aacaggaaaa attttaataa ttgtactgag agaaactgct tacgtacaca ttgcagatca | 3240 |
| aatatttgga gttaaaatgt tagtctacat agatgggtga ttgtaacttt attgccatta | 3300 |
| aaagatttca aattgcattc atgcttctgt gtacacataa tgaaaatgg gcaaataatg | 3360 |
| aagatctctc cttcagtctg ctctgtttaa ttctgctgtc tgctcttctc taatgctgcg | 3420 |
| tccctaattg tacacagttt agtgatatct aggagtataa agttgtcgcc catcaataaa | 3480 |
| aatcacaaag ttggtttaaa aaaaaaaaaa aaaaaaaaa | 3520 |

<210> SEQ ID NO 9
<211> LENGTH: 3399
<212> TYPE: DNA
<213> ORGANISM: Homo sapiens

<400> SEQUENCE: 9

| | |
|---|---|
| ctccccgcgc cccgcggcgc gcggccagtg cgcaggcgcg gcggccgatg cgagtgtgta | 60 |
| tgtgcgggcg agaagatggc ggcggcgggg gaagcagcgt gagcagccgg aggatcgcgg | 120 |
| agtcccaatg aaacgggcag ccatggccct ccacagcccg cagtatattt ttggagattt | 180 |
| tagccctgat gaattcaatc aattcttgt gactcctcga tcttcagttg agcttcctcc | 240 |

| | |
|---|---|
| atacagtgga acagttctgt gtggcacaca ggctgtggat aaactacctg atggacaaga | 300 |
| atatcagaga attgagtttg gtgtcgatga agtcattgaa cccagtgaca ctttgccgag | 360 |
| aacccccagc tacagtattt caagcacact gaaccctcag gcccctgaat ttattctcgg | 420 |
| ttgtacagct tccaaaataa cccctgatgg tatcactaaa gaagcaagct atggctccat | 480 |
| cgactgccag tacccaggct ctgccctcgc tttggatgga agttctaatg tggaggcgga | 540 |
| agttttggaa aatgatggtg tctcaggtgg tcttggacaa agggagcgta aaagaagaa | 600 |
| aaagcggcca cctggatatt acagctattt gaaagatggt ggcgatgata gtatctccac | 660 |
| agaagccctg gtcaatggcc atgccaattc agcagtcccg aacagtgtca gtgcaggga | 720 |
| tgcagaattt atgggtgaca tgccccgtc agttacgccc aggacttgta acagccccca | 780 |
| gaactccaca gactctgtca gtgacattgt gcctgacagt cctttccccg gagcactcgg | 840 |
| cagtgacacc aggactgcag ggcagccaga ggggggcccc ggggctgatt ttggtcagtc | 900 |
| ctgcttccct gcagaggctg gcagagacac cctgtcaagg acagctgggg ctcagccctg | 960 |
| cgttggtacc gatactactg aaaaccttgg agttgctaat ggacaaatac ttgaatcctc | 1020 |
| gggtgagggc acagctacca acggggtgga gttgcacacc acggaaagca tagacttgga | 1080 |
| cccaaccaaa cccgagagtg catcacctcc tgctgacggc acgggctctg catcaggcac | 1140 |
| ccttcctgtc agccagccca gtcctgggc cagcctctttt catgattcta agccctcttc | 1200 |
| ctcctcgccg gtggcctatg tggaaactaa gtattcccct cccgccatat ctcccctggt | 1260 |
| ttctgaaaag caggttgaag tcaaagaagg gcttgttccg gtttcagagg atcctgtagc | 1320 |
| cataaagatt gcagagttgc tggagaatgt aaccctaatc cataaaccag tgtcgttgca | 1380 |
| accccgtggg ctgatcaata aagggaactg gtgctacatt aatgctacac tgcaggcatt | 1440 |
| ggttgcttgc ccgccgatgt accacctgat gaagttcatt cctctgtatt ccaaagtgca | 1500 |
| aaggccttgt acgtcaacac ccatgataga cagctttgtt cggctaatga atgagttcac | 1560 |
| taatatgcca gtacctccaa aaccccgaca agctcttgga gataaaatcg tgagggatat | 1620 |
| tcgccctgga gctgcctttg agcccacata tatttacaga ctcctgacag ttaacaagtc | 1680 |
| aagcctgtct gaaaagggtc gacaagaaga tgctgaggaa tacttaggct tcattctaaa | 1740 |
| tggacttcat gaggaaatgt tgaacctaaa gaagcttctc tcaccaagta atgaaaaact | 1800 |
| tacgatttcc aacggcccca aaaccactc ggtcaatgaa gaagagcagg aagaacaagg | 1860 |
| tgaaggaagc gaggatgaat gggaacaagt gggcccccgg aacaagactt ccgtcacccg | 1920 |
| ccaggcggat tttgttcaga ctccaatcac cggcattttt ggtggacaca tcaggtctgt | 1980 |
| ggtttaccag cagagttcaa aagaatctgc cactttgcag ccattttca cgttgcagtt | 2040 |
| ggatatccag tcagacaaga tacgcacagt ccaggatgca ctggagagct ggtggcaag | 2100 |
| agaatctgtc caaggttata ccacaaaaac caaacaagag gttgagataa gtcgaagagt | 2160 |
| gactctggaa aaactccctc ctgtcctcgt gctgcacctg aaacgattcg tttatgagaa | 2220 |
| gactggtggg tgccagaagc ttatcaaaaa tattgaatat cctgtggact tggaaattag | 2280 |
| taaagaactg ctttctccag gggttaaaaa taagaatttt aaatgccacc gaacctatcg | 2340 |
| gctctttgca gtggtctacc atcacggcaa cagtgcgacg gcggccatt acactacaga | 2400 |
| cgtcttccag atcggtctga atggctggct gcgcatcgat gaccagacag tcaaggtgat | 2460 |
| caaccagtac caggtggtga aaccaactgc tgaacgcaca gcctacctcc tgtattaccg | 2520 |
| ccgagtggac ctgctgtaaa ccctgtgtgc gctgtgtgtg cgcccagtgc cgcttcgta | 2580 |
| ggacaccacc tcacactcac ttcccgcctc tctttagtgg ctctttagag agaaactctt | 2640 |

```
tctcccttg caaaaatggg ctagaatgaa aaggagatgc cttggggttc gtgcacaaca    2700
cagcttctgt tgactctaac ttccaaatca aaatcatttg gttgaaacag actgttgctt    2760
gattttagaa aatacacaaa aacccatatt tctgaaataa tgctgattcc tgagataaga    2820
aagtggattt gatccccagt ctcattgctt agtagaataa atcctgcacc agcaacaaca    2880
cttgtaaatt tgtgaaaatg aattttatct ttccttaaaa aagaaatttt ttaatccatc    2940
acacttttct tccctaccct ttagttttg ataaatgata aaaatgagcc agttatcaaa    3000
gaagaactag ttcttacttc aaaagaaaaa taaacataaa aaataagttg ctggttccta    3060
acaggaaaaa ttttaataat tgtactgaga gaaactgctt acgtacacat tgcagatcaa    3120
atatttggag ttaaaatgtt agtctacata gatgggtgat tgtaacttta ttgccattaa    3180
aagatttcaa attgcattca tgcttctgtg tacacataat gaaaaatggg caaataatga    3240
agatctctcc ttcagtctgc tctgtttaat tctgctgtct gctcttctct aatgctgcgt    3300
ccctaattgt acacagttta gtgatatcta ggagtataaa gttgtcgccc atcaataaaa    3360
atcacaaagt tggtttaaaa aaaaaaaaaa aaaaaaaa                              3399
```

<210> SEQ ID NO 10
<211> LENGTH: 863
<212> TYPE: PRT
<213> ORGANISM: Homo sapiens

<400> SEQUENCE: 10

Met Gln Arg Arg Gly Ala Leu Phe Gly Met Pro Gly Gly Ser Gly Gly
1               5                   10                  15

Arg Lys Met Ala Ala Gly Asp Ile Gly Glu Leu Leu Val Pro His Met
            20                  25                  30

Pro Thr Ile Arg Val Pro Arg Ser Gly Asp Arg Val Tyr Lys Asn Glu
        35                  40                  45

Cys Ala Phe Ser Tyr Asp Ser Pro Asn Ser Glu Gly Gly Leu Tyr Val
    50                  55                  60

Cys Met Asn Thr Phe Leu Ala Phe Gly Arg Glu His Val Glu Arg His
65                  70                  75                  80

Phe Arg Lys Thr Gly Gln Ser Val Tyr Met His Leu Lys Arg His Val
                85                  90                  95

Arg Glu Lys Val Arg Gly Ala Ser Gly Gly Ala Leu Pro Lys Arg Arg
            100                 105                 110

Asn Ser Lys Ile Phe Leu Asp Leu Asp Thr Asp Asp Leu Asn Ser
        115                 120                 125

Asp Asp Tyr Glu Tyr Glu Asp Glu Ala Lys Leu Val Ile Phe Pro Asp
    130                 135                 140

His Tyr Glu Ile Ala Leu Pro Asn Ile Glu Glu Leu Pro Ala Leu Val
145                 150                 155                 160

Thr Ile Ala Cys Asp Ala Val Leu Ser Ser Lys Ser Pro Tyr Arg Lys
                165                 170                 175

Gln Asp Pro Asp Thr Trp Glu Asn Glu Leu Pro Val Ser Lys Tyr Ala
            180                 185                 190

Asn Asn Leu Thr Gln Leu Asp Asn Gly Val Arg Ile Pro Pro Ser Gly
        195                 200                 205

Trp Lys Cys Ala Arg Cys Asp Leu Arg Glu Asn Leu Trp Leu Asn Leu
    210                 215                 220

Thr Asp Gly Ser Val Leu Cys Gly Lys Trp Phe Phe Asp Ser Ser Gly
225                 230                 235                 240

```
Gly Asn Gly His Ala Leu Glu His Tyr Arg Asp Met Gly Tyr Pro Leu
            245                 250                 255

Ala Val Lys Leu Gly Thr Ile Thr Pro Asp Gly Ala Asp Val Tyr Ser
        260                 265                 270

Phe Gln Glu Glu Pro Val Leu Asp Pro His Leu Ala Lys His Leu
    275                 280                 285

Ala His Phe Gly Ile Asp Met Leu His Met His Gly Thr Glu Asn Gly
290                 295                 300

Leu Gln Asp Asn Asp Ile Lys Leu Arg Val Ser Glu Trp Glu Val Ile
305                 310                 315                 320

Gln Glu Ser Gly Thr Lys Leu Lys Pro Met Tyr Gly Pro Gly Tyr Thr
            325                 330                 335

Gly Leu Lys Asn Leu Gly Asn Ser Cys Tyr Leu Ser Ser Val Met Gln
            340                 345                 350

Ala Ile Phe Ser Ile Pro Glu Phe Gln Arg Ala Tyr Val Gly Asn Leu
            355                 360                 365

Pro Arg Ile Phe Asp Tyr Ser Pro Leu Asp Pro Thr Gln Asp Phe Asn
370                 375                 380

Thr Gln Met Thr Lys Leu Gly His Gly Leu Leu Ser Gly Gln Tyr Ser
385                 390                 395                 400

Lys Pro Pro Val Lys Ser Glu Leu Ile Glu Gln Val Met Lys Glu Glu
                405                 410                 415

His Lys Pro Gln Gln Asn Gly Ile Ser Pro Arg Met Phe Lys Ala Phe
            420                 425                 430

Val Ser Lys Ser His Pro Glu Phe Ser Ser Asn Arg Gln Gln Asp Ala
        435                 440                 445

Gln Glu Phe Phe Leu His Leu Val Asn Leu Val Glu Arg Asn Arg Ile
450                 455                 460

Gly Ser Glu Asn Pro Ser Asp Val Phe Arg Phe Leu Val Glu Glu Arg
465                 470                 475                 480

Ile Gln Cys Cys Gln Thr Arg Lys Val Arg Tyr Thr Glu Arg Val Asp
                485                 490                 495

Tyr Leu Met Gln Leu Pro Val Ala Met Glu Ala Ala Thr Asn Lys Asp
            500                 505                 510

Glu Leu Ile Ala Tyr Glu Leu Thr Arg Arg Glu Ala Glu Ala Asn Arg
        515                 520                 525

Arg Pro Leu Pro Glu Leu Val Arg Ala Lys Ile Pro Phe Ser Ala Cys
530                 535                 540

Leu Gln Ala Phe Ser Glu Pro Glu Asn Val Asp Asp Phe Trp Ser Ser
545                 550                 555                 560

Ala Leu Gln Ala Lys Ser Ala Gly Val Lys Thr Ser Arg Phe Ala Ser
                565                 570                 575

Phe Pro Glu Tyr Leu Val Val Gln Ile Lys Lys Phe Thr Phe Gly Leu
            580                 585                 590

Asp Trp Val Pro Lys Lys Phe Asp Val Ser Ile Asp Met Pro Asp Leu
        595                 600                 605

Leu Asp Ile Asn His Leu Arg Ala Arg Gly Leu Gln Pro Gly Glu Glu
    610                 615                 620

Glu Leu Pro Asp Ile Ser Pro Pro Ile Val Ile Pro Asp Asp Ser Lys
625                 630                 635                 640

Asp Arg Leu Met Asn Gln Leu Ile Asp Pro Ser Asp Ile Asp Glu Ser
                645                 650                 655
```

Ser Val Met Gln Leu Ala Glu Met Gly Phe Pro Leu Glu Ala Cys Arg
            660                 665                 670

Lys Ala Val Tyr Phe Thr Gly Asn Met Gly Ala Glu Val Ala Phe Asn
        675                 680                 685

Trp Ile Ile Val His Met Glu Glu Pro Asp Phe Ala Glu Pro Leu Thr
    690                 695                 700

Met Pro Gly Tyr Gly Ala Ala Ser Ala Gly Ala Ser Val Phe Gly
705                 710                 715                 720

Ala Ser Gly Leu Asp Asn Gln Pro Pro Glu Ile Val Ala Ile Ile
                725                 730                 735

Thr Ser Met Gly Phe Gln Arg Asn Gln Ala Ile Gln Ala Leu Arg Ala
            740                 745                 750

Thr Asn Asn Asn Leu Glu Arg Ala Leu Asp Trp Ile Phe Ser His Pro
        755                 760                 765

Glu Phe Glu Glu Asp Ser Asp Phe Val Ile Glu Met Glu Asn Asn Ala
    770                 775                 780

Asn Ala Asn Ile Ile Ser Glu Ala Lys Pro Glu Gly Pro Arg Val Lys
785                 790                 795                 800

Asp Gly Ser Gly Thr Tyr Glu Leu Phe Ala Phe Ile Ser His Met Gly
                805                 810                 815

Thr Ser Thr Met Ser Gly His Tyr Ile Cys His Ile Lys Lys Glu Gly
            820                 825                 830

Arg Trp Val Ile Tyr Asn Asp His Lys Val Cys Ala Ser Glu Arg Pro
        835                 840                 845

Pro Lys Asp Leu Gly Tyr Met Tyr Phe Tyr Arg Arg Ile Pro Ser
850                 855                 860

<210> SEQ ID NO 11
<211> LENGTH: 7933
<212> TYPE: DNA
<213> ORGANISM: Homo sapiens

<400> SEQUENCE: 11
gctcgctggc gccgccgccg ccggcagacc ccgcgctccg gctccggctc ggctcgctcg    60
gctccggtgc gcgccgaggc catgcagcgc cggggcgccc tgttcggcat gccgggcggc   120
agcggaggca ggaagatggc tgcaggagac atcggcgagc tgctagtgcc ccacatgccc   180
acgatccgcg tgcccaggtc cggcgacagg gtctacaaga acgagtgcgc cttctcctac   240
gactctccca attctgaagg tggactctat gtatgcatga atacattttt ggcctttgga   300
agggaacatg ttgaaagaca ttttcgaaaa actggacaga gtgtatacat gcacctgaaa   360
agacatgtgc gagagaaggt aagagggggcg tctggtggag cgttaccaaa aaggaggaat   420
tccaagattt ttttagatct agatactgat gacgatttaa atagcgacga ttatgaatat   480
gaagatgaag ccaaacttgt tatattccca gatcactatg aaatagcact accaaatatt   540
gaggagttac cagccctggt aacaattgct tgtgatgcag ttctcagctc aaaatctcca   600
tacagaaagc aggacccaga cacgtgggaa atgaattgc cagtatctaa atatgccaac   660
aacctcaccc agctggacaa tggagtcagg attcctccaa gtggttggaa gtgtgccaga   720
tgcgacctgc gagaaaacct ctggttgaat ctgactgacg ctctgtcct gtgtggaaag   780 tggttctttg acagctctgg gggcaacggg catgcgctgg agcattacag agacatgggc   840
tacccactag ccgtgaaact gggaaccatc actcctgacg gggcagatgt ttattctttt   900
caagaagaag aacctgtttt ggatcctcat ttggccaagc acttagcgca ttttggaatt   960

-continued

```
gatatgcttc atatgcatgg gacagagaat gggctccagg acaatgacat caagctgagg      1020
gtcagtgagt gggaagtgat ccaggagtcg ggcacgaaac tgaagccaat gtatggtcct      1080
ggctacacgg gtctgaagaa cctgggcaac agctgctatc tcagctctgt catgcaggcc      1140
atcttcagca tcccagaatt ccagagagcg tatgtaggaa accttcccag aatatttgac      1200
tactcgcctt tagatccaac acaagatttc aacacacaga tgactaagtt aggacatggc      1260
cttctctcag gccagtattc aaagcctccg gtgaaatctg aactcattga acaggtgatg      1320
aaggaggagc acaagccaca gcagaacggg atctctccgc gcatgtttaa ggcctttgta      1380
agcaagagcc acccggaatt ctcctctaac aggcagcaag atgcccagga attcttcttg      1440
cacctggtga atctagtaga gaggaaccgc atcggctcag aaaacccaag cgatgttttt      1500
cgttttttgg tggaagaacg cattcagtgc tgtcagaccc ggaaagtccg ctacacggag      1560
agggtggatt acctgatgca gttacctgtg gccatggagg cggcaaccaa caaggatgaa      1620
ctgatcgctt atgaactaac gagaagggaa gcagaagcaa acagaagacc ccttcctgag      1680
ttggtacgtg ccaagatacc atttagtgcc tgccttcagg ccttctctga accagaaaat      1740
gttgatgatt tctggagcag tgccctacaa gcaaagtctg cgggtgtgaa acatctcgc      1800
tttgcttcat tccctgaata cttggtagtg cagataaaga agttcacttt tggtcttgac      1860
tgggttccca aaaaatttga tgtttctatt gatatgccag acctacttga tatcaaccat      1920
ctccgagcca gggggttaca gccaggagag gaagaacttc cagacatcag ccccccata      1980
gtcattcctg atgactcaaa agatcgcctg atgaaccaat tgatagaccc atcagacatc      2040
gatgagtcat cagtgatgca gctggccgag atgggtttcc cgctggaagc atgtcgcaag      2100
gctgtgtact tcactggaaa tatgggcgcc gaggtggcct tcaactggat cattgttcac      2160
atggaagagc cagattttgc tgagccgctg accatgcctg gttatggagg ggcagcttct      2220
gctggagcct ctgtttttgg tgcttctgga ctggataacc aacctccaga ggaaatcgta      2280
gctatcatca cctccatggg atttcagcga aatcaggcta ttcaggcact acgagcaacg      2340
aataataacc tggaaagagc actggattgg atctttagcc accctgagtt tgaagaagac      2400
agtgattttg tgattgagat ggagaataat gccaatgcaa acattattc tgaggccaag      2460
cccgaaggac ctagagtcaa ggatggatct ggaacatatg agctatttgc attcatcagt      2520
cacatgggaa catccacaat gagtggtcat tacatttgcc atatcaaaaa ggaaggaaga      2580
tgggtgattt acaatgacca caaagttgt gcctcagaaa ggcccctaa agacctgggc      2640
tacatgtact tttaccgcag gataccaagc taaacctcaa atataaaaat tggcgaaaag      2700
aagccatacg cctttttaat ttgccaaaaa aaaaagaag aagaagaagt tgaaacaact      2760
agacatgaag gaatatatgg ggtatttatc gtttatttaa agagcacgat cagttgacac      2820
cttctgaaat agaactgaga agaaatttct attagtgatg atacactatt atattgtaga      2880
tagtttttat aaatgttcaa aaagatgatg atatttaaaa acaaaaaaag tattcatatt      2940
gctggtggag gatctgccat cagcacatca aaaatgggga tgtgccccca gccctctatt      3000
ttgctttggg ggtcagtgat agtggcctct ggagaaacca ataatgtgg ccagtggtgt      3060
ggccttaccc acaacaaatg aaaagccac ttgtgtttca tatagaaaat cagcagttgg      3120
gtggggcttt atttgtgaca taatttttt catgacatac aataatttct gatgtatcca      3180
tgtagatatt atgctctgtc cataatagag cctctgcaat gaaagatatt tttaatttgt      3240
cacattaaaa ttcataatac gattgtgtga atgtgtgtga gactgactga gagtgtgaga      3300
cttttactag aaaagtgagt ccactagaaa atctgtgaca agttggtttt taaagtctga      3360
```

```
acagttgata ttaagcatat ctgaaaaaag caagtaaata ttttaacaaa actatgactc    3420
aggaaccttc gagaagatta gttccccact tagatttta aggagtaaaa agggctgagt     3480
tatgccttta agtgctgtca agaattcact tgggtttggg acatttgctg gtgtaatgct    3540
agatgcccac agcagcataa tattgtactt tgtcaaaggt aggtaaattc tctgtttctc    3600
agcagcccct tccccaaaag gtatggtgtt tattttagt aaaaatagct aatctctttt     3660
taccatctca catgataact ctttggagtc atgtcaagtg ccccaaattt gtctgtgatt    3720
ttcccatctc tgagctcttt atctgcctcc gtttccttgt ttttctgggg ccagagtctc    3780
atctctgcct ttttttggtg tatcaccttc tgacttgcct tcattgcttg tctgatgtga    3840
ccaacagtgt gatcttggac acactaagga tttagatgc aaagaaactt tatacaacat     3900
tatgaaagac tatcctttcc attttggtta tttcagcatt ttagttgcaa cctgggatta    3960
gattagagtt ccaacgtga tgaaaagtgg aatgatagca ttctataatt tccataattt     4020
tcctactggt ccgtaccaaa ttctagagtc tctggagttg ctatttcaga gtatttggtc    4080
aaacgaaaaa gaatttattg ctgtctgttt aacatgtatt tgtttggttg aaaggatctt    4140
tttagaaact gtaggaaaat aaacagaacc aaccaggtga aacaaagcac agacattggg    4200
ttaggatgta gtgagttgtg aacaatcagg attctgggtg tgatgggggt ccctgtctca    4260
taggtgatcc tttggtgcca tgtgaccgag agacatggtg tctaaggccc atggcctgga    4320
gacctgggtg ctgctcctag ctgactgtgg accttgggca agtccttcat ccgtcctgtg    4380
cctcactgtc ctcatctgaa caatggtatg atgacacctg ccctctcttt caatcatgct    4440
ttgaggatac agtgagattg gttacagtga accttcaatg agtagaatgt ggtatgccat    4500
ggtgggttgt agtagatggt gctccctgcc ttttctcctc tgttttcctc aatttgggaa    4560
caaatgagat tggcagaagg agggagctca cggtgcagta cttttctacc aaagtgtgcc    4620
cactggtgtc acctcctaat gttaacttgg atttcctaaa gcagtcccac tctgttatga    4680
gagtcactga ctcccgtgga catccccaca gtaagcagcc ttacaaaatc cagtcccctt    4740
agggcagagt gagtgtcata gaataatgac tccaaaccca cgtcaaaaat ggcttgtttt    4800
cagcgatgtt ataaaacaaa ggcctgtttt ttggaattgg gggtgactgg gtggtttgga    4860
ttgaaatgtg gacaaagata gcatgtgtat tttgaataaa ataaaaattt tgtaataaaa    4920
cttttaaaaa tcagtgatgt aaaatcaata tttaagacta taggctataa attgtttgat    4980
ttcattaact agccctttg atgcctagac atgttgtaaa aaaattgtgc tatggctgcc     5040
ttttcttctg ccccacaaca caaagggcta tttctacaag gcaaagtttt gtatatgtgc    5100
tattctttac ttcagattga gagttgggaa aaactggagt aaataatggg tttcttactt    5160
gcttaaaagc atatttatat gtgtatctca atatatacaa ggcaggttcc cctataaaag    5220
tctggaatgt actgcttaat tttacacttg tgtagacacg attatttgtg actgaaaagt    5280
ggaataacgt gtggattttg tcaactcatt atcagtctgt tagcagtcct ctatgtgagg    5340
catggtggtc taattgtgaa attctccctg tatatgggtg tctgtgtgaa agacagcact    5400
ttcttcctgt aaatatcttt tgatatccat ttatgtagaa ttccaatgaa tatgtctttg    5460
gaaaaggtaa tgtatcaaag ttttttatttt gccaattgat ctaaatgccc ataactaa     5520 tcagaaatcc agtttggttc agattgggat tttcttttaa agaaaaaaaa agtatgcaga    5580
aaagactatt ggaagaatca tgtgttagtg acactttaca tcaacgttgc ttcaatattt    5640
tggaattgac caggctgctt tctcctacct gcaagagaat gtgcctgaca tttcccagtg    5700
```

```
cttactttgg gctataggaa gtccagcggg gatagctcga gcctcttgct ccctgagtca      5760
tttattccct ttacctgaac agagccttac ctgcaattca tagtgagagc acctgggtct      5820
gtatcctgac tccactctaa gtgaggtggg actgaatcac tgtacctctc tgggccttt      5880 catttgaaac aagtgggtta gactagatta gctccaaagt cctctcttgc cctaacattt      5940
tatttttatt ttcctgtggt taccactagg gtctgacacg taaaatgtga gggatcactt      6000
agaggtttgg atgttatatt tttgcattgt tacagcttat actccccagt tgaggacctg      6060
tgtcattctt agtggcccca cgacccctct gtttgtattc ctgctccact tatctatact      6120
tttttgggta atcatcccac ttttttttt tcttgagatg gagtctcgct gtgttgccaa      6180
ggctggagta cagtggtgca atctcagctc actgcagcct cctcccgggt tcaagtgatt      6240
ctcctgcctc agcttcccaa gtagctggga ttactggcgc acgccactac gcccagctaa      6300 ttttttgtatt tttagtagag acagggtttt gccatgttgg ccaggctggt cttgaactct      6360
tgacctcaac ctgcctcagc ctcccaaagt gctgggatta cacgcatgag ctaccgcgtc      6420
cagccccact ttttttctac tcttgaaaaa aacaactttc tagtccatga ggtactttgg      6480
ctccatcccc ctcaaaaaca aaacaaaaaa tccatttaaa gtgtcctcct agaaaagcct      6540
cagaactgcc ttcaactaca tctgtcacct ttatagaata ttttgaaatt ctggaagagg      6600
atgggaaaca aaattctaat ttagctagag ctgtgatccc caaataagtg ctgacaaaat      6660
tgtctaccac agaaaggccg tccttgtcat cttgtaggca tcactgctgc taaatcacat      6720
cagtacatgc cttctgtggg gagatggcag ggggcagggg caggaccagg ggatgggatt      6780
agataaagtg tgataatgtc ctttagataa aagaaatcct acgctataga acaaggttct      6840
gtactcttga gttggtgtct gagatcacct gcacagtgtt acagagattt tccactccat      6900
aaatcactct aaaagagttt gcataagact cggtagacct gtgctattca atgtggcagt      6960
caacagccat atgtggcgat gactactcaa agtttggctt gttcaaatcg agactgtgtt      7020
gtacacatac aatacacacc agattttgaa ggcttggtac caaaaaggaa tttaaaatat      7080
ttcaccaata tttcatattg ataacatgct gaaatgacac tattttggat gtactaagta      7140
aaatattaac aatttaatat atttatataa ttgaaattaa aattcttttc acccattttt      7200
atttttttaa aaatgtggcc cctaaagaac ttcaaattag acatgtggat aacgttatac      7260
ttctattgga cagccccact ctagacttac atggtgtggg gtaggcagtg aaatccgtaa      7320
ataggaaacg caattctgca aagtatctaa atagacagaa acaacacaaa tattttgct      7380 gggagtcagga gcactgtgag gcacagaaca tctcccagaa agcagatttt ttttttctgc      7440
cgaaaaacca atatatatat gtatgatccc aattaaaaga caaaagcaaa tgagccccaa      7500
actgcctgtc ttcagctttg cctgggagct gctacctttg ctcttctagc atcttctagg      7560
taccaaggat attagccact tgagggtgtt gggcatattt gtttcattgt aggcaaaatc      7620
ctcttgtggt ttcccctccc caggtattgt tgagtctgtt caaagctggg tgtgttgaaa      7680
cactgcacaa atcctgccac tcttgatgtg ccgcttgtct cagccttggc agaggctgag      7740
tctgttcctg tgcccacctg tccagcaggt tttgatgttg gctcctgaaa gagtttgtat      7800 ttatttttatt ttgcactagt cacagttgtt gttaaactgt atcaaatgtt ttgggagatt      7860
atttgcctga gatggaaaga gagatggatg atttattgct tcaattgttt taaattaaaa      7920
gctattctca caa                                                        7933
```

<210> SEQ ID NO 12
<211> LENGTH: 2632

<212> TYPE: DNA
<213> ORGANISM: Homo sapiens

<400> SEQUENCE: 12

```
gtacaaaaaa gcaggctcca ccatgcagcg ccggggcgcc ctgttcggca tgccgggcgg      60
cagcggaggc aggaagatgg ctgcaggaga catcggcgag ctgctagtgc cccacatgcc     120
cacgatccgc gtgcccaggt ccggcgacag ggtctacaag aacgagtgcg ccttctccta     180
cgactctccc aattctgaag gtggactcta tgtatgcatg aatacatttt tggcctttgg     240
aagggaacat gttgaaagac attttcgaaa aactggacag agtgtataca tgcacctgaa     300
aagacatgtg cgagagaagg taagaggggc gtctggtgga gcgttaccaa aaaggaggaa     360
ttccaagatt ttttagatc tagatactga tgacgattta aatagcgacg attatgaata     420
tgaagatgaa gccaaacttg ttatattccc agatcactat gaaatagcac taccaaatat     480
tgaggagtta ccagccctgg taacaattgc ttgtgatgca gttctcagct caaaatctcc     540
atacagaaag caggacccag acacgtggga aaatgaattg ccagtatcta aatatgccaa     600
caacctcacc cagctggaca atggagtcag gattcctcca agtggttgga agtgtgccag     660
atgcgacctg cgagaaaacc tctggttgaa tctgactgac ggctctgtcc tgtgtggaaa     720
gtggttcttt gacagctctg ggggcaacgg gcatgcgctg gagcattaca gagacatggg     780
ctacccacta gccgtgaaac tgggaaccat cactcctgac ggggcagatg tttattcttt     840
tcaagaagaa gaacctgttt tggatcctca tttggccaag cacttagcgc attttggaat     900
tgatatgctt catatgcatg ggacagaaa tgggctccag acaatgaca tcaagctgag     960
ggtcagtgag tgggaagtga tccaggagtc gggcacgaaa ctgaagccaa tgtatggtcc    1020
tggctacacg ggtctgaaga acctgggcaa cagctgctat ctcagctctg tcatgcaggc    1080
catcttcagc atcccagaat tccagagagc gtatgtagga aaccttccca gaatatttga    1140
ctactcgcct ttagatccaa cacaagattt caacacacag atgactaagt taggacatgg    1200
ccttctctca ggccagtatt caaagcctcc ggtgaaatct gaactcattg aacaggtgat    1260
gaaggaggag cacaagccac agcagaacgg gatctctccg cgcatgttta aggccttttgt    1320
aagcaagagc caccccggaat tctcctctaa caggcagcaa gatgcccagg aattcttctt    1380
gcacctggtg aatctagtag agaggaaccg catcggctca gaaaacccaa gcgatgtttt    1440
tcgttttttg gtggaagaac gcattcagtg ctgtcagacc cggaaagtcc gctacacgga    1500
gagggtggat tacctgatgc agttacctgt ggccatggag gcggcaacca acaaggatga    1560
actgatcgct tatgaactaa cgagaaggga agcagaagca acagaagac cccttcctga    1620
gttggtacgt gccaagatac catttagtgc ctgccttcag gccttctctg aaccagaaaa    1680
tgttgatgat ttctggagca gtgccctaca agcaaagtct gcgggtgtga aaacatctcg    1740
ctttgcttca ttccctgaat acttggtagt gcagataaag aagttcactt ttggtcttga    1800
ctgggttccc aaaaaatttg atgtttctat tgatatgcca gacctacttg atatcaacca    1860
tctccgagcc agggggttac agccaggaga ggaagaactt ccagacatca gccccccat     1920
agtcattcct gatgactcaa agatcgcct gatgaaccaa ttgatagacc catcagacat    1980
cgatgagtca tcagtgatgc agctggccga gatgggtttc ccgctggaag catgtcgcaa    2040
ggctgtgtac ttcactggaa atatgggcgc cgaggtggcc ttcaactgga tcattgttca    2100
catggaagag ccagattttg ctgagccgct gaccatgcct ggttatggag gggcagcttc    2160
tgctggagcc tctgttttttg gtgcttctgg actggataac caacctccag aggaaatcgt    2220
```

```
                                         -continued agctatcatc acctccatgg gatttcagcg aaatcaggct attcaggcac tacgagcaac    2280
gaataataac ctggaaagag cactggattg gatctttagc caccctgagt ttgaagaaga    2340
cagtgatttt gtgattgaga tggagaataa tgccaatgca aacattattt ctgaggccaa    2400
gcccgaagga cctagagtca aggatggatc tggaacatat gagctatttg cattcatcag    2460
tcacatggga acatccacaa tgagtggtca ttacatttgc catatcaaaa aggaaggaag    2520
atgggtgatt tacaatgacc acaaagtttg tgcctcagaa aggcccccta aagacctggg    2580
ctacatgtac ttttaccgca ggataccaag ctaggaccca gctttcttgt ac            2632

<210> SEQ ID NO 13
<211> LENGTH: 19
<212> TYPE: DNA
<213> ORGANISM: Artificial sequence
<220> FEATURE:
<223> OTHER INFORMATION: Synthetic construct

<400> SEQUENCE: 13
aaatcgtcat cagtatcta                                                   19

<210> SEQ ID NO 14
<211> LENGTH: 19
<212> TYPE: DNA
<213> ORGANISM: Artificial sequence
<220> FEATURE:
<223> OTHER INFORMATION: Synthetic construct

<400> SEQUENCE: 14
ccatgtgaac aatgatcca                                                   19
```